United States Patent [19]
Hashimoto

[11] Patent Number: 5,317,093
[45] Date of Patent: May 31, 1994

[54] BISAZO COMPOUNDS USEFUL AS ORGANIC PHOTOCONDUCTIVE MATERIALS

[75] Inventor: Mitsuru Hashimoto, Numazu, Japan

[73] Assignee: Ricoh Company, Ltd., Tokyo, Japan

[21] Appl. No.: 762,462

[22] Filed: Sep. 19, 1991

[30] Foreign Application Priority Data

Sep. 20, 1990 [JP] Japan ................. 2-248708
Oct. 15, 1990 [JP] Japan ................. 2-273431
Nov. 29, 1990 [JP] Japan ................. 2-326046
Jul. 29, 1991 [JP] Japan ................. 3-188716

[51] Int. Cl.$^5$ .......................... C07C 245/10
[52] U.S. Cl. ..................... 534/658; 534/561
[58] Field of Search .......................... 534/658

[56] References Cited

U.S. PATENT DOCUMENTS 4,481,271 11/1984 Hashimoto et al. ........... 534/658 X
4,939,058 7/1990 Shibata et al. ................ 534/658 X Primary Examiner—Mary C. Lee
Assistant Examiner—Fiona T. Powers
Attorney, Agent, or Firm—Oblon, Spivak, McClelland, Maier & Neustadt

[57] ABSTRACT

Bisazo compounds, useful as organic photoconductive materials, having formula (I) or (II) are disclosed:

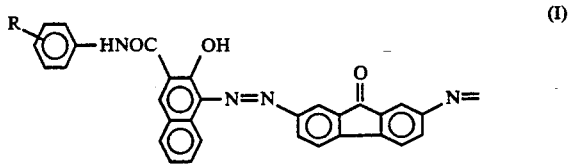

(I)

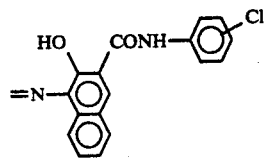

wherein R represents hydrogen, an alkyl group having 1 to 4 carbon atoms, an alkoxy group having 1 to 4 carbon atoms or a nitro group;

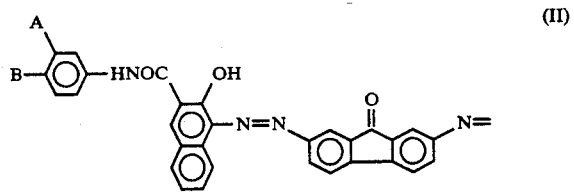

(II)

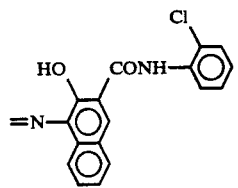

wherein A and B independently represent hydrogen or chloride provided that either A or B represents chloride.

3 Claims, 20 Drawing Sheets

BISAZO COMPOUNDS USEFUL AS ORGANIC PHOTOCONDUCTIVE MATERIALS

BACKGROUND OF THE INVENTION

1. Field of the Invention

The present invention relates to bisazo compounds, and more particularly to bisazo compounds useful as organic photoconductive materials in the field of electrophotography.

2. Discussion of Background

It is conventionally known that some azo compounds are useful as charge generating pigments when used in a charge generation layer of a two-layered type photoconductor, which is one embodiment of the electrophotographic photoconductors. The above-mentioned two-layered type photoconductor can be prepared by forming a charge generation layer and a charge transport layer successively on an electroconductive support. More specifically, the charge generation layer is formed on the support in such a manner that a charge generating pigment capable of generating charge carriers when exposed to light is vacuum-deposited on the support, or a solution of such a charge generating pigment or a dispersion prepared by dispersing finely-divided particles of the charge generating pigment in a resin solution is coated on the support. On the thus formed charge generation layer, the charge transport layer comprising a charge transporting material and a binder resin is overlaid. This charge transport layer has a function of effectively accepting and transporting the charge carriers generated in the charge generation layer.

As azo compounds used as the photoconductive materials in the photoconductor of the above-mentioned type, for example, benzidine-type bisazo compounds disclosed in Japanese Laid-Open Patent Applications 47-37543 and 52-55643, and stilbene-type bisazo compounds disclosed in Japanese Laid-Open Patent Application 52-8832 are conventionally known.

The two-layered photoconductors employing the above-mentioned conventional azo compounds, however, are poor in sensitivity, so that they are not suitable for use with a high-speed copying apparatus.

SUMMARY OF THE INVENTION

Accordingly, an object of this invention is to provide bisazo compounds which are effective as photoconductive materials for use in the electrophotographic photoconductor, particularly in the above-mentioned two-layered type photoconductor.

The object of the present invention can be achieved by bisazo compounds having formula (I) or having formula (II):

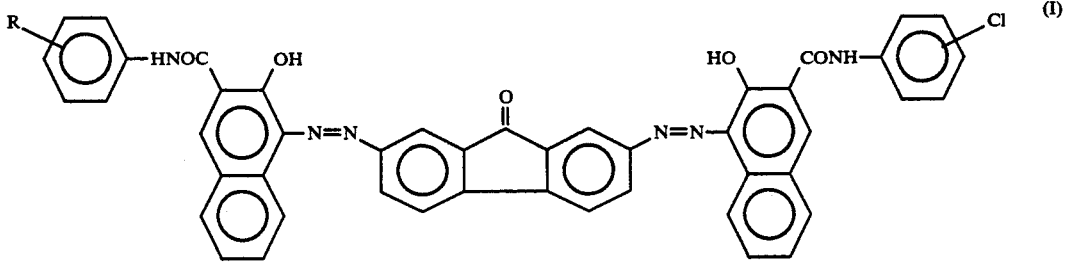

wherein R represents hydrogen, an alkyl group having 1 to 4 carbon atoms, an alkoxyl group having 1 to 4 carbon atoms or a nitro group;

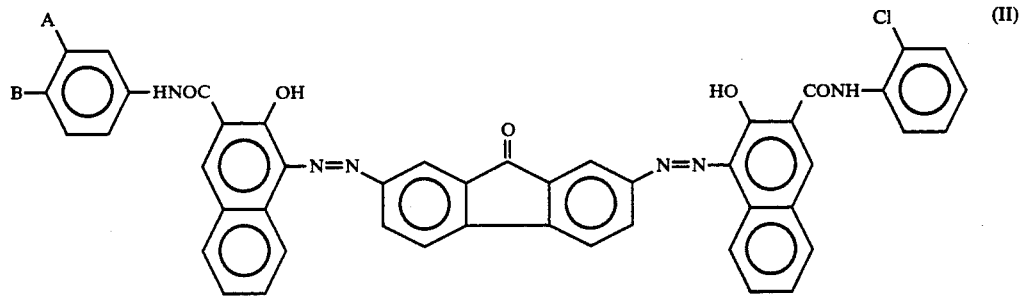

wherein A and B independently represent hydrogen or chloride provided that either A or B represents chloride.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
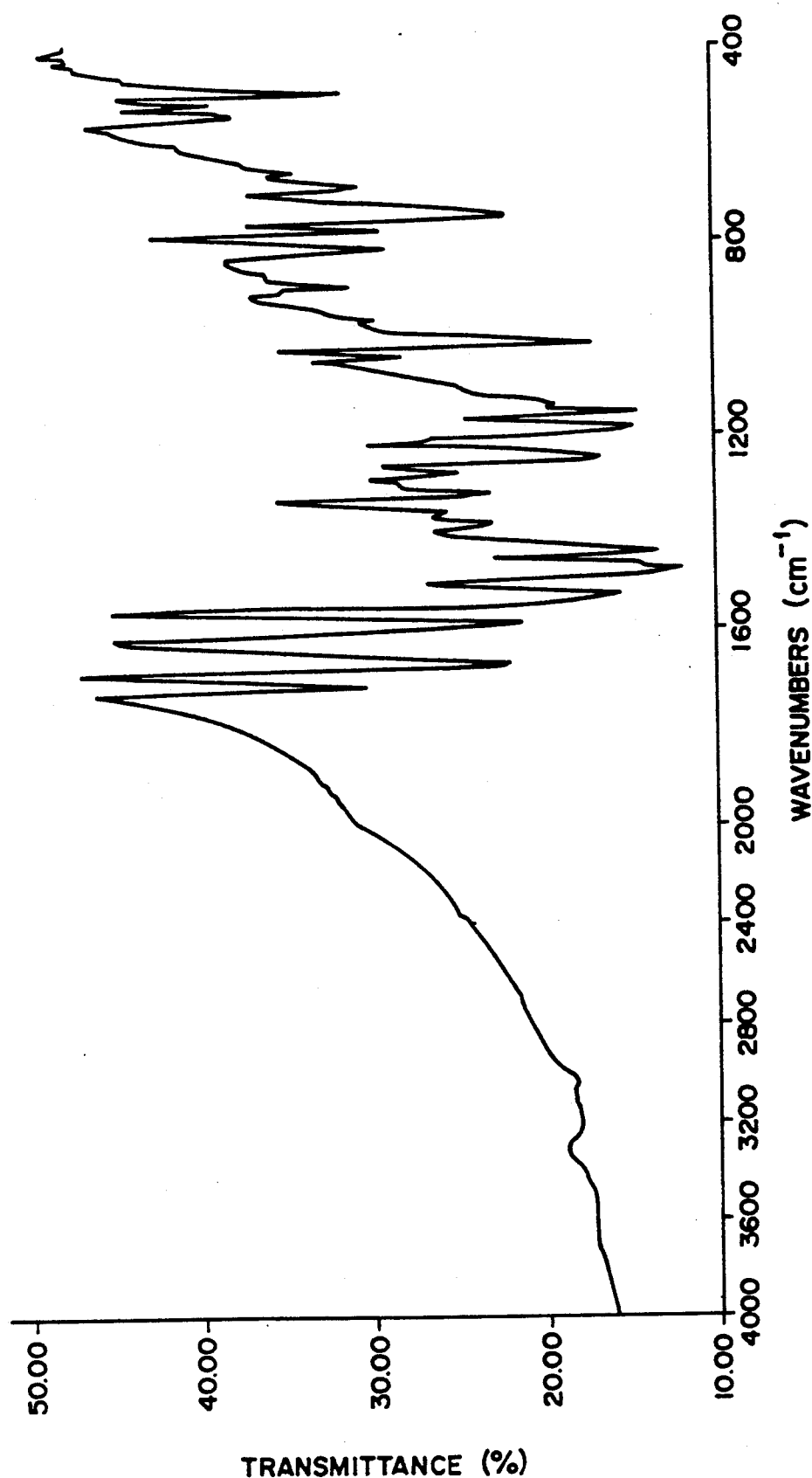
FIG. 1 is an infrared absorption spectrum of a bisazo compound according to the present invention, which is obtained in Example 1.

The bisazo compounds represented by formulas (I) and (II) are effective as charge generating materials for use in the charge generation layer of the two-layered type electrophotographic photoconductor, and in a photoconductive layer of a single-layered type photoconductor, in which photoconductive layer a charge generating material and a charge generating material are dispersed in a resin. In addition, the above bisazo compounds are useful as the photoconductive materials for use in a photoconductive layer of the electrophotographic photoconductor prepared by dispersing the photoconductive material in a binder resin.

The bisazo compound of the present invention is represented by the following formula (I) or (II):

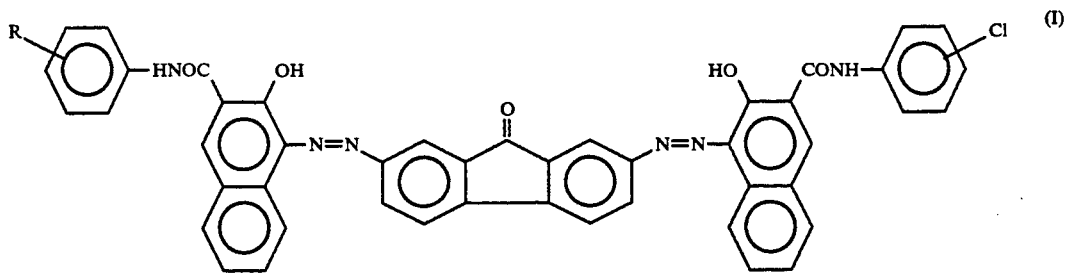

(I)

wherein R represents hydrogen, an alkyl group having 1 to 4 carbon atoms, an alkoxyl group having 1 to 4 carbon atoms or a nitro group;

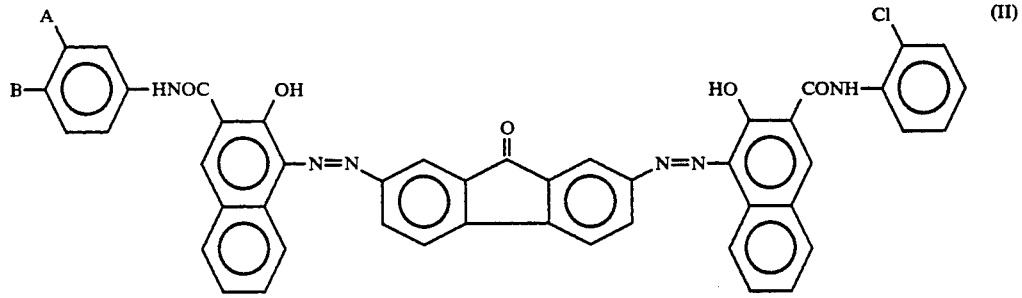

(II)

wherein A and B independently represent hydrogen or chloride provided that either A or B represents chloride.

Preferable examples of the bisazo compound represented by the formula (I) are as follows:

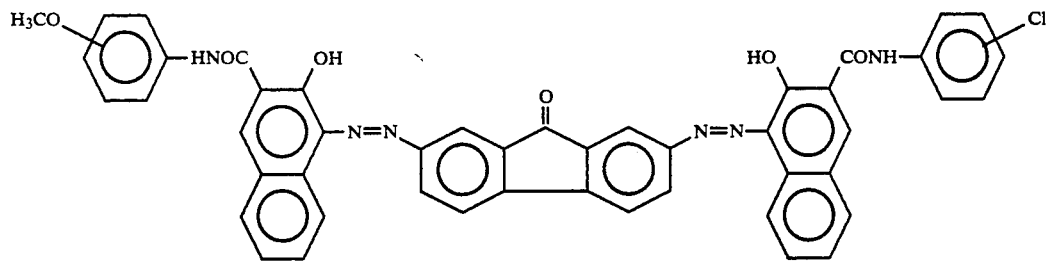

and

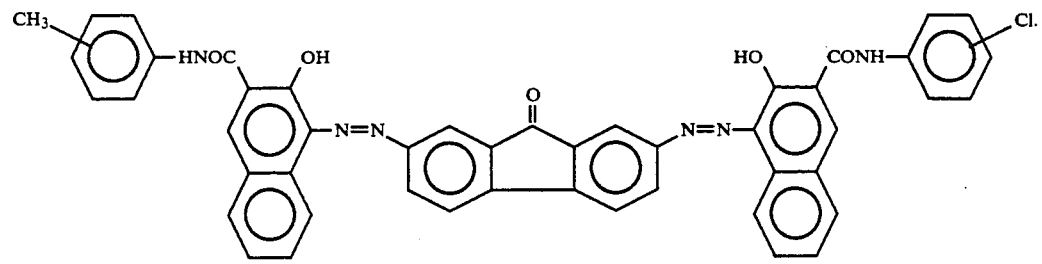

Specific examples of the bisazo compound of formula (I) according to the present invention are as follows:

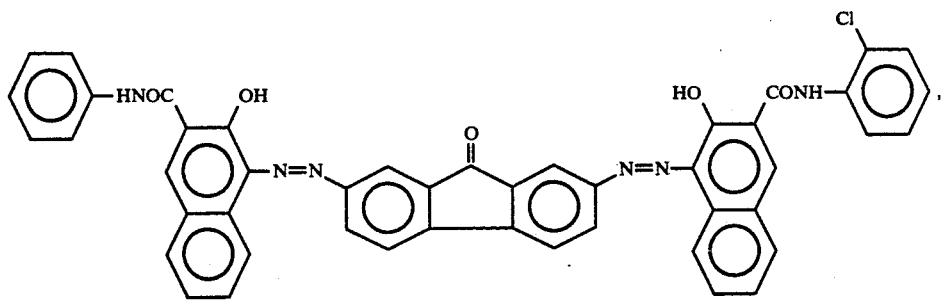
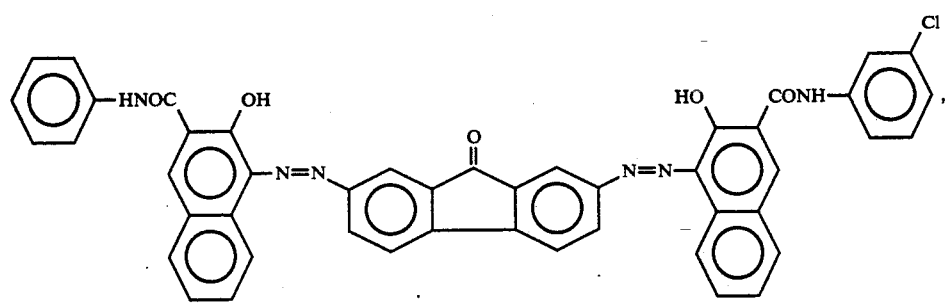
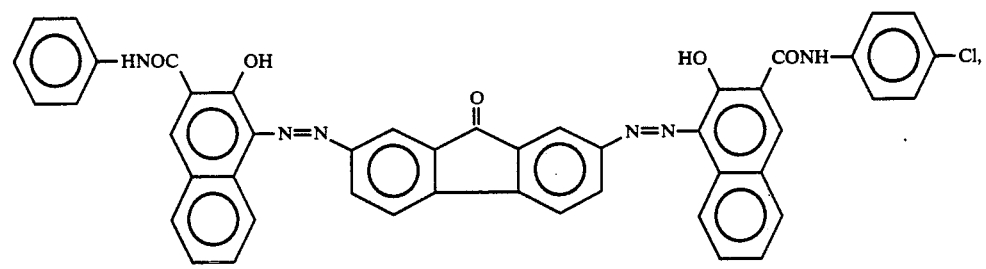
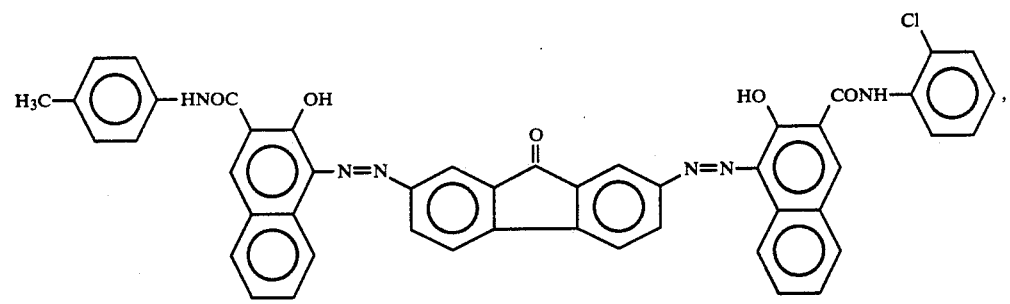
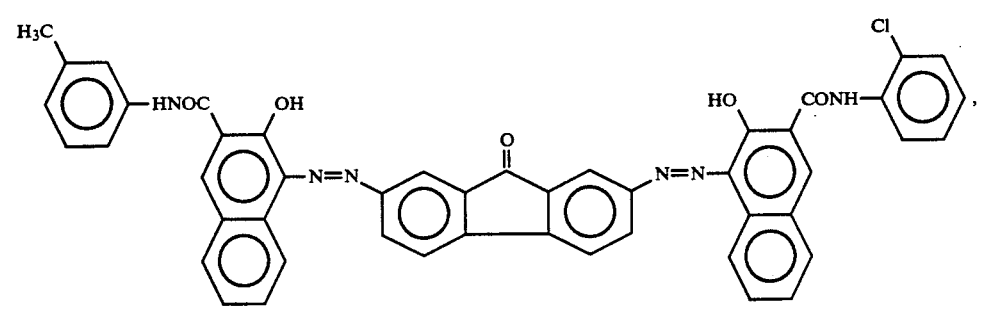

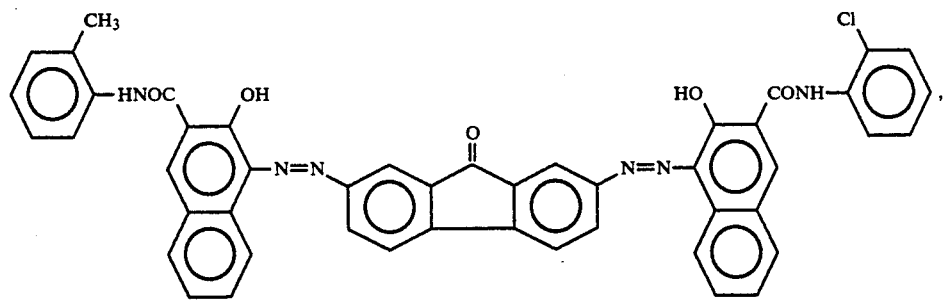
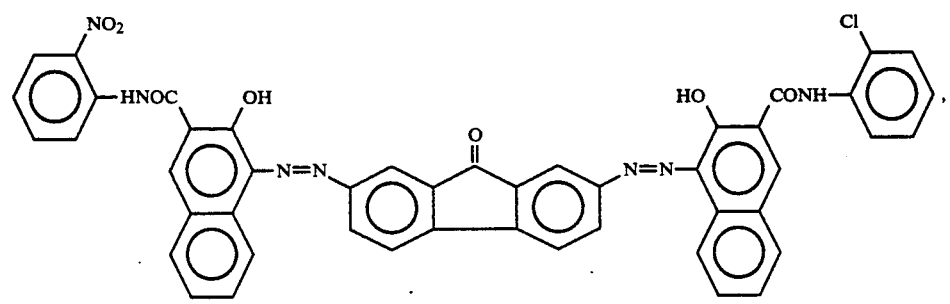
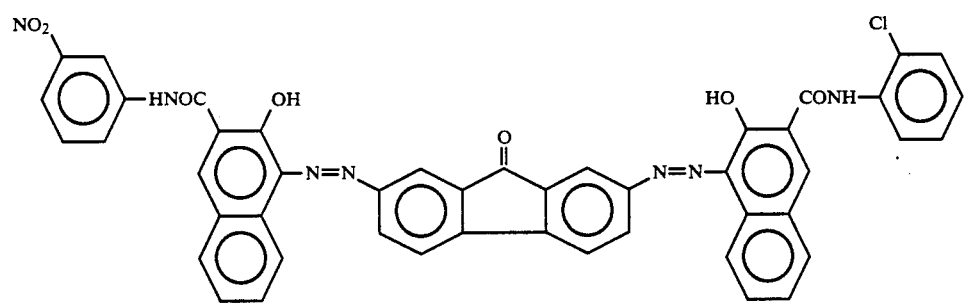
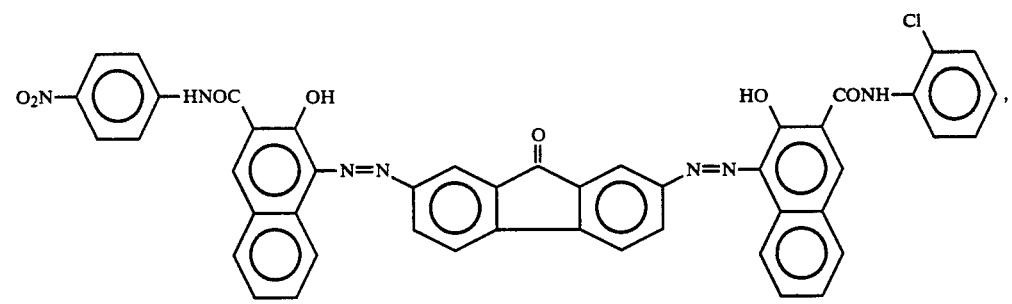
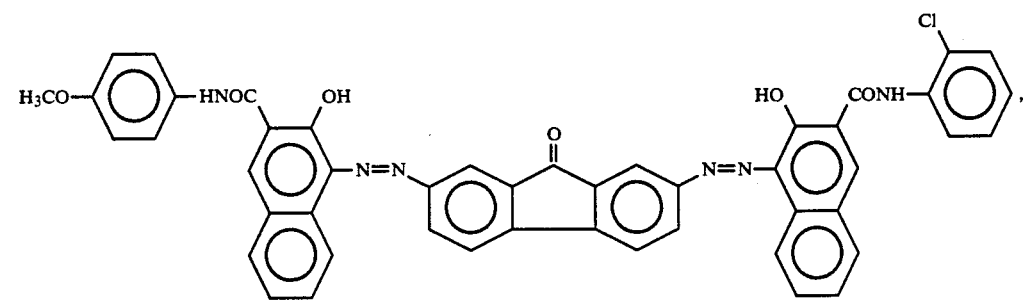

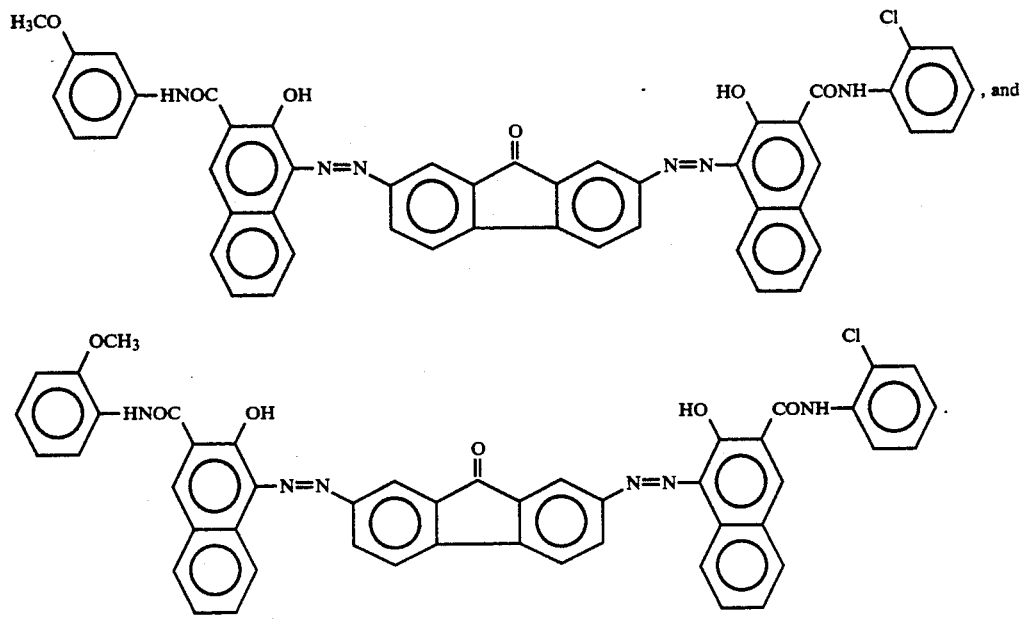

Preferable examples of the bisazo compound represented by the formula (II) are as follows:

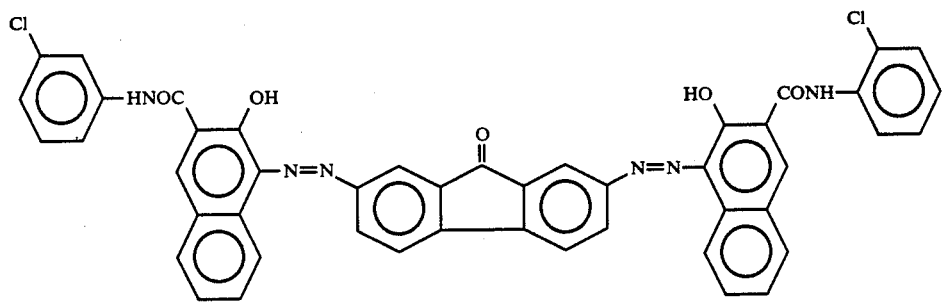

and

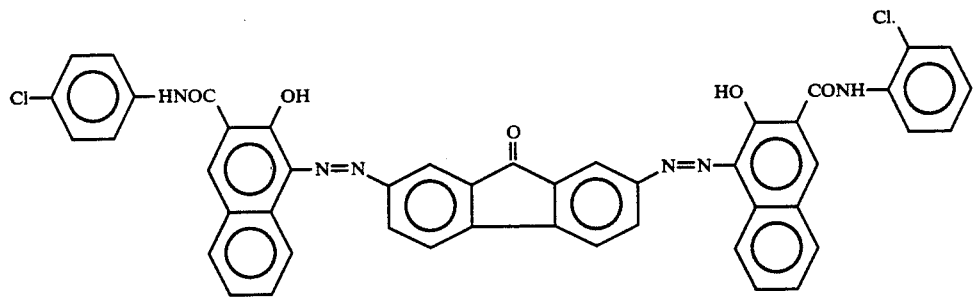

The above-mentioned bisazo compounds of formula (I) according to the present invention can be prepared by a step-by-step method in which a diazonium salt compound of the following formula (I-1) is allowed to react with a compound of the following formula (I-2), and the thus obtained intermediate product is allowed to react with a compound having the following formula (I-3). Alternatively, the diazonium compound having formula (I-1) may first be allowed to react with the compound having formula (I-3), followed by allowing the obtained intermediate product to react with the compound having formula (I-2).

(I-1)

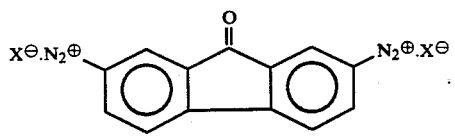

wherein X represents as anionic functional group.

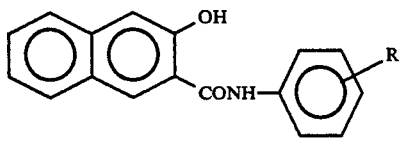

wherein R represents hydrogen, an alkyl group having 1 to 4 carbon atoms, an alkoxyl group having 1 to 4 carbon atoms or a nitro group.

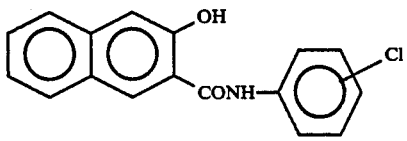

Furthermore, the bisazo compound (I) of the present invention can also be prepared by isolating a diazonium salt compound (I-4) or (I-5), represented by the following formula, which is prepared by the first coupling reaction between the compound of (I-1) and the compound (I-2) or between the compound of (I-1) and the compound (I-3), respectively in the above-mentioned step-by-step method. Then, the diazonium salt compound (I-4) may be allowed to react with the corresponding coupler (I-3), while the diazonium salt compound (I-5) may be allowed to react with the corresponding coupler (I-2).

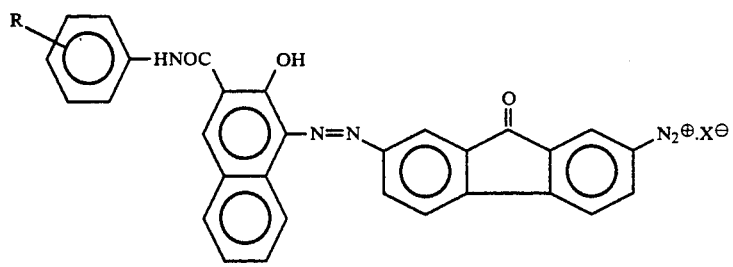

wherein X represents an anionic functional group; and R represents hydrogen, an alkyl group having 1 to 4 carbon atoms, an alkoxyl group having 1 to 4 carbon atoms or a nitro group.

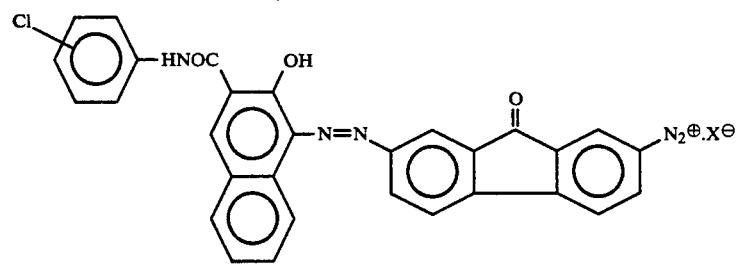

wherein X represents an anionic functional group.

In the formula (I) and other formulas (I-2) and (I-4) representing the starting material and the intermediate product of the bisazo compound of formula (I), R represents hydrogen, an alkyl group having 1 to 4 carbon atoms, an alkoxyl group having 1 to 4 carbon atoms or a nitro group.

As the alkyl group, a methyl group, an ethyl group, a propyl group and a butyl group are preferable.

In the formulas (I-1), (I-4) and (I-5), X represents an anionic functional group, such as BF4, perchlorate, iodate, chloride, bromide, sulfate, hexafluorophosphate, hexafluoroantimonate, periodate and p-toluenesulfonate.

In the aforementioned step-by-step method, the first coupling reaction is carried out in such a fashion that the coupler (I-2) or (I-3) is dissolved in an organic solvent such as N,N-dimethylformamide (DMF) or dimethyl sulfoxide (DMSO) and the diazonium salt compound of formula (I-1) is added to the above-prepared solution of the coupler. The first coupling reaction is completed when a basic material such as an aqueous solution of sodium acetate or an organic amine is added to the reaction mixture if necessary. It is preferable that the reaction temperature in the first coupling reaction be in the range from about −20° C. to about 40° C.

In the second coupling reaction, the other coupler (I-2) or (I-3), which is not used in the first coupling reaction, is further added to the reaction mixture obtained in the first coupling reaction. The second coupling reaction can also be completed when a basic material such as an aqueous solution of sodium acetate or an organic amine is added to the reaction mixture if necessary.

Alternatively, to the reaction mixture obtained in the first coupling reaction, water or an acidic aqueous solution such as an aqueous solution of dilute hydrochloric acid is added when necessary to isolate the diazonium salt compound of formula (I-4) or (I-5) by filtration. When water or the acidic aqueous solution is added to the above-mentioned reaction mixture, it is required to sufficiently cool the reaction mixture so as not to decompose the diazonium salt compound (I-4) or (I-5) synthesized in the reaction. It is desirable that the reaction mixture be cooled at 10° C. or less. Then, in the case where the diazonium salt compound (I-4) is isolated, it may be allowed to react with the coupler (I-3) in the same manner as in the first coupling reaction of the step-by-step method as mentioned above. On the other hand, in the case where the diazonium salt compound (I-5) is isolated, it may be allowed to react with the coupler (I-2), likewise.

From the reaction mixtures obtained by any method, separating crystals are removed from the mixture by filtration, and purified by an appropriate method, for instance, by washing with water or/and an organic solvent or recrystallization. Thus, bisazo compounds of the present invention can be obtained.

The above-mentioned bisazo compounds of formula (II) according to the present invention can be prepared by a step-by-step method in which a diazonium salt compound of the following formula (II-1) is allowed to react with a compound of the following formula (II-2), and the thus obtained intermediate product is allowed to react with a compound having the following formula (II-3). Alternatively, the diazonium compound having formula (II-1) may first be allowed to react with the compound having formula (II-3), followed by allowing the obtained intermediate product to react with the compound having formula (II-2).

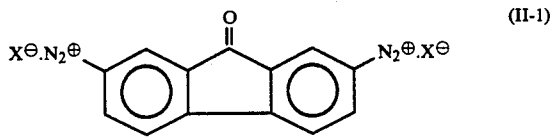
(II-1)

wherein X represents an anionic functional group.

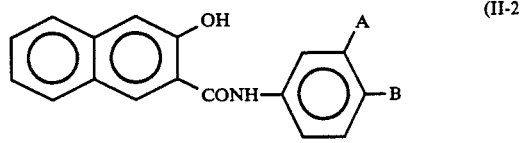
(II-2)

wherein A and B independently represent hydrogen or chloride provided that either A or B represents chloride.

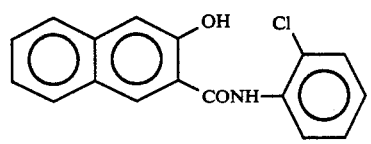
(II-3)

Furthermore, the bisazo compound (II) of the present invention can also be prepared by isolating a diazonium salt compound (II-4) or (II-5), represented by the following formula, which is prepared by the first coupling reaction between the compound of (II-1) and the compound (II-2) or between the compound of (II-1) and the compound (II-3), respectively in the above-mentioned step-by-step method. Then, the diazonium salt compound (II-4) may be allowed to react with the corresponding coupler (II-3), while the diazonium salt compound (II-5) may be allowed to react with the corresponding coupler (II-2).

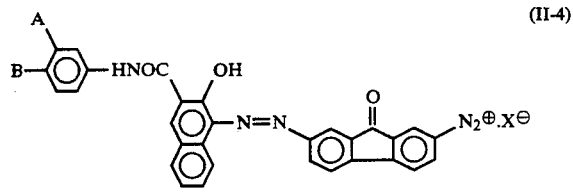
(II-4)

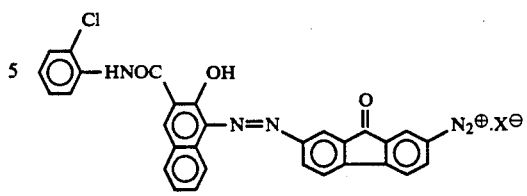
(II-5)

wherein X represents an anionic functional group; and A and B independently represent hydrogen or chloride provided that either A or B represents chloride.

In the formulas (II-1), (II-4) and (II-5), X represents an anionic functional group, such as tetrafluoroborate, perchlorate, iodate, chloride, bromide, sulfate, hexafluorophosphate, hexafluoroantimonate, periodate and p-toluenesulfonate.

The reactions to prepare the bisazo compound of formula (II) can be carried out in the same manner as in the case where the bisazo compound of formula (I) is prepared.

Other features of this invention will become apparent in the course of the following description of exemplary embodiments, which are given for illustration of the invention and are not intended to be limiting thereof.

EXAMPLE 1

0.74 g (2.5 mmol) of 2-hydroxy-3-(2-chlorophenyl)-carbamoylnaphthalene having formula (I-3a) was dissolved in 100 ml of DMF.

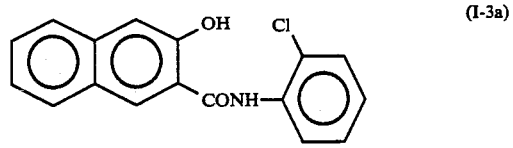
(I-3a)

To the above-prepared solution, 1.02 g (2.5 mmol) of 9-fluorenone-2,7-bisdiazonium bistetrafluoroborate having formula (I-1a) was added at a room temperature. The reaction mixture was stirred for 10 minutes at room temperature.

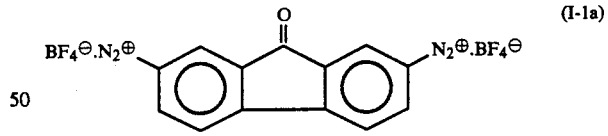
(I-1a)

100 ml of DMF solution containing 0.66 g (2.5 mmol) of 2-hydroxy-3-phenylcarbamoylnaphthalene having formula (I-2a) was added to the above reaction mixture, with the addition thereto of 8 ml of 10.5% aqueous solution of sodium acetate, followed by stirring for 2 hours at room temperature.

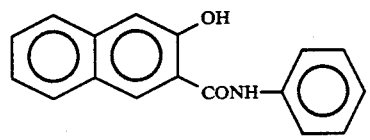
(I-2a)

A precipitated reaction product in the reaction mixture was removed by filtration. The reaction product was washed with 200 ml of DMF of 80° C. three times, and with 200 ml of water twice, and then dried at 120° C. under reduced pressure. Thus, a bisazo compound having formula (Ia) according to the present invention was obtained in a 63% yield. The melting point of the thus obtained bisazo compound was 280° C. or more.

EXAMPLE 4

The procedure for preparation of the bisazo compound (Ia) used in Example 1 was repeated except that 9-fluorenone-2,7-bisdiazonium bistetrafluoroborate having formula (I-1a) was first allowed to react with

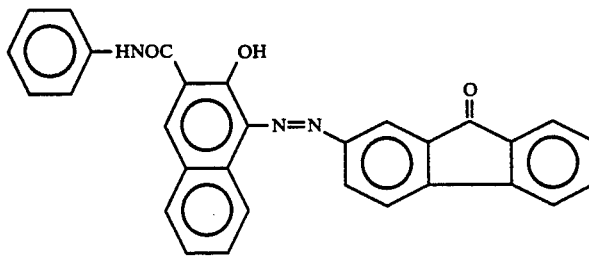

(Ia)

The results of the elemental analysis of the thus obtained bisazo compound (Ia) were as follows:

|  | % C | % H | % N |
|---|---|---|---|
| Calculated | 71.16 | 3.68 | 10.60 |
| Found | 71.05 | 3.57 | 10.33 |

FIG. 1 shows an infrared spectrum of the above obtained bisazo compound, taken by use of a KBr tablet.

EXAMPLE 2

The procedure for preparation of the bisazo compound (Ia) used in Example 1 was repeated except that the reaction temperature was changed from the room temperature to a temperature ranging from 10° to 15° C., so that a bisazo compound of formula (Ia) according 2-hydroxy-3phenylcarbamoylnaphthalene having formula (I-2a), and the thus obtained reaction mixture was then allowed to react with 2-hydroxy-3-(2-chlorophenyl)-carbamoylnaphthalene having formula (I-3a), so that a bisazo compound of formula (Ia) according to the present invention was obtained.

EXAMPLE 5

The procedure for preparation of the bisazo compound (Ia) used in Example 1 was repeated except that 0.66 g of 2-hydroxy-3-phenylcarbamoylnaphthalene having formula (I-2a) was replaced by 0.69 g (2.5 mmol) of 2-hydroxy-3-(3-methylphenyl)carbamoylnaphthalene (I-2b), so that a bisazo compound of formula (Ib) according to the present invention was obtained in a 56% yield. The melting point of the thus obtained bisazo compound was 280° C. or more.

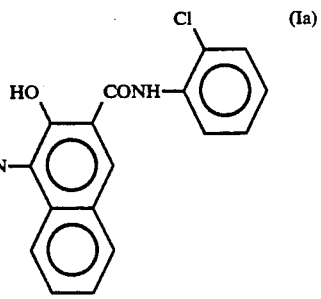

(I-2b)

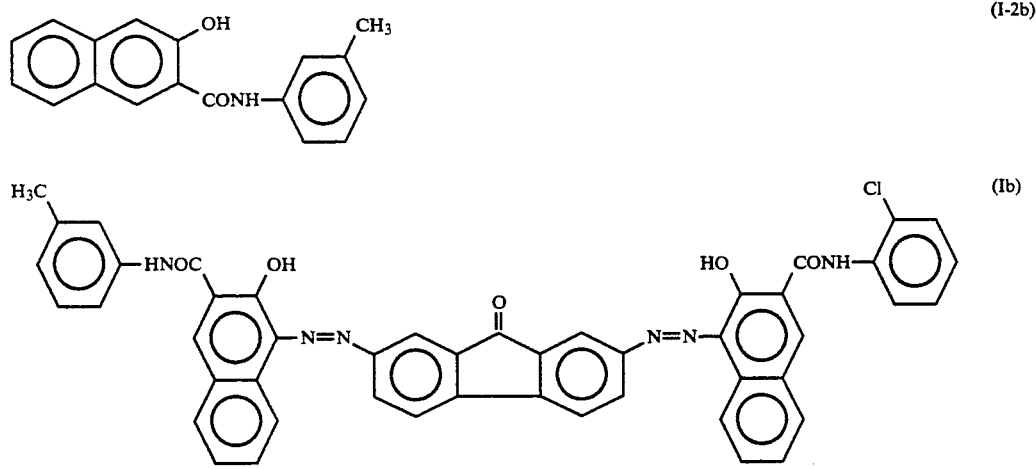

(Ib)

to the present invention was obtained.

EXAMPLE 3

The procedure for preparation of the bisazo compound (Ia) used in Example 1 was repeated except that the reaction temperature was changed from the room temperature to a temperature ranging from 0° to 5° C., so that a bisazo compound of formula (Ia) according to the present invention was obtained.

The results of the elemental analysis of the thus obtained bisazo compound (Ib) were as follows:

|  | % C | % H | % N |
|---|---|---|---|
| Calculated | 71.42 | 3.87 | 10.41 |
| Found | 71.14 | 3.85 | 10.15 |

Figure 2:
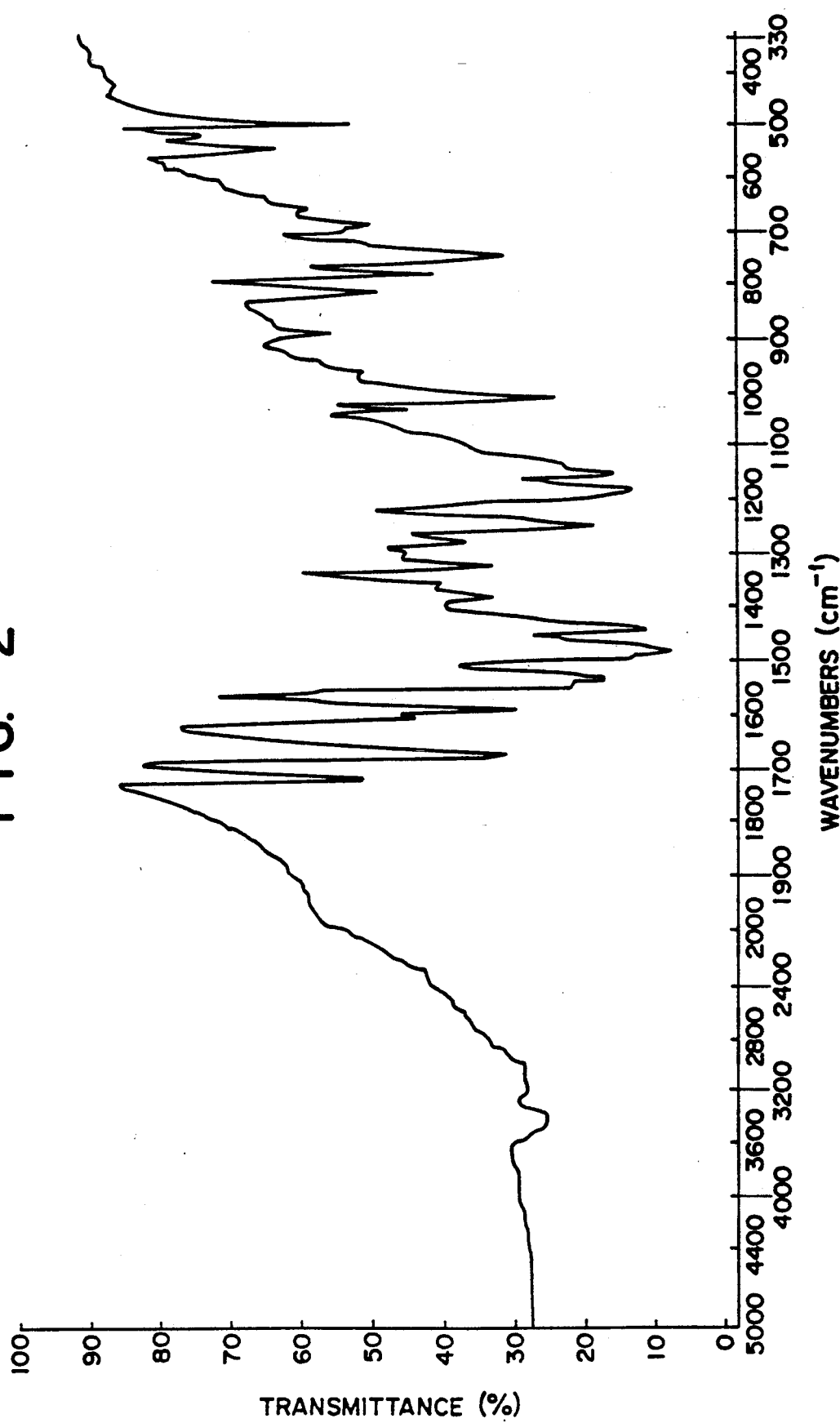
FIGS. 2 to 14 are infrared absorption spectra of bisazo compounds according to the present invention, which are obtained in Examples 5, 9, 13, 17, 21, 25, 29, 33, 37, 41, 45, 49 and 53, respectively.

FIG. 2 shows an infrared spectrum of the above obtained bisazo compound, taken by use of a KBr tablet.

EXAMPLE 6

The procedure for preparation of the bisazo compound (Ib) used in Example 5 was repeated except that the reaction temperature was changed from the room temperature to a temperature ranging from 10° to 15° C., so that a bisazo compound of formula (Ib) according to the present invention was obtained.

EXAMPLE 7

The procedure for preparation of the bisazo compound (Ib) used in Example 5 was repeated except that the reaction temperature was changed from the room temperature to a temperature ranging from 0° to 5° C., so that a bisazo compound of formula (Ib) according to the present invention was obtained.

EXAMPLE 8

The procedure for preparation of the bisazo compound (Ib) used in Example 5 was repeated except that 9-fluorenone-2,7-bisdiazonium bistetrafluoroborate having formula (I-1a) was first allowed to react with 2-hydroxy-3-(3-methylphenyl)carbamoylnaphthalene (I-2b), and the thus obtained reaction mixture was then allowed to react with 2-hydroxy-3-(2-chlorophenyl)-carbamoylnaphthalene having formula (I-3a), so that a bisazo compound of formula (Ib) according to the present invention was obtained.

EXAMPLE 9

The procedure for preparation of the bisazo compound (Ia) used in Example 1 was repeated except that 0.66 g of 2-hydroxy-3-phenylcarbamoylnaphthalene having formula (I-2a) was replaced by 0.69 g (2.5 mmol) of 2-hydroxy-3-(4methylphenyl)carbamoylnaphthalene (I-2c), so that a bisazo compound of formula (Ic) according to the present invention was obtained in a 65% yield. The melting point of the thus obtained bisazo compound was 280° C. or more.

Figure 3:
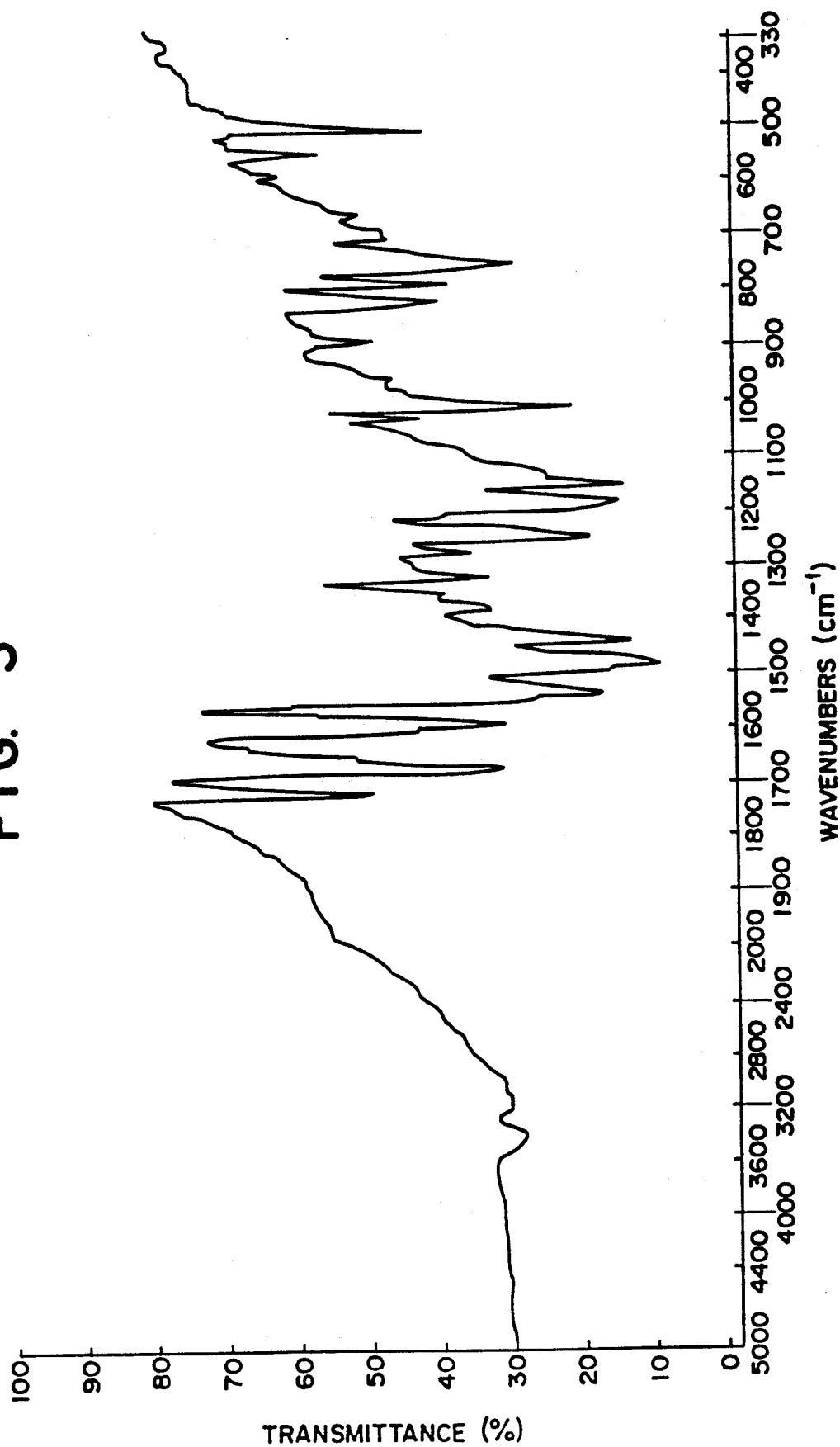

FIG. 3 shows an infrared spectrum of the above obtained bisazo compound, taken by use of a KBr tablet.

EXAMPLE 10

The procedure for preparation of the bisazo compound (Ic) used in Example 9 was repeated except that the reaction temperature was changed from the room temperature to a temperature ranging from 10° to 15° C., so that a bisazo compound of formula (Ic) according to the present invention was obtained.

EXAMPLE 11

The procedure for preparation of the bisazo compound (Ic) used in Example 9 was repeated except that the reaction temperature was changed from the room temperature to a temperature ranging from 0° to 5° C., so that a bisazo compound of formula (Ic) according to the present invention was obtained.

EXAMPLE 12

The procedure for preparation of the bisazo compound (Ic) used in Example 9 was repeated except that 9-fluorenone-2,7-bisdiazonium bistetrafluoroborate having formula (I-1a) was first allowed to react with 2-hydroxy-3-(4-methylphenyl)carbamoylnaphthalene (I-2c), and the thus obtained reaction mixture was then allowed to react with 2-hydroxy-3-(2-chlorophenyl)-carbamoylnaphthalene having formula (I-3a), so that a bisazo compound of formula (Ic) according to the present invention was obtained.

EXAMPLE 13

The procedure for preparation of the bisazo compound (Ia) used in Example 1 was repeated except that 0.74 g (2.5 mmol) of 2-hydroxy-3-(2-chlorophenyl)carbamoylnaphthalene having formula (I-3a) was replaced by 0.66 g (2.5 mmol) of 2-hydroxy-3-phenylcarbamoylnaphthalene having formula (I-2a) and that 0.66 g (2.5 mmol) of 2-hydroxy-3-phenylcarbamoylnaphthalene

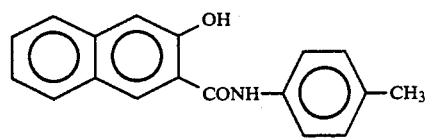

(I-2c)

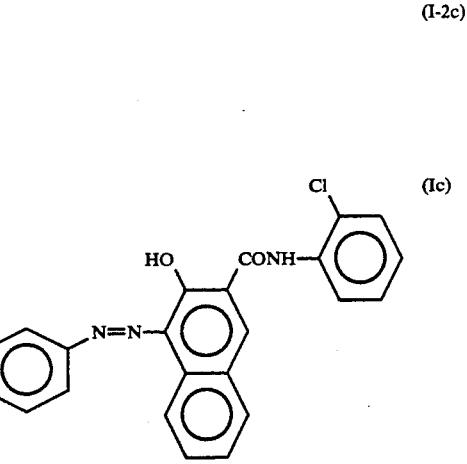

(Ic)

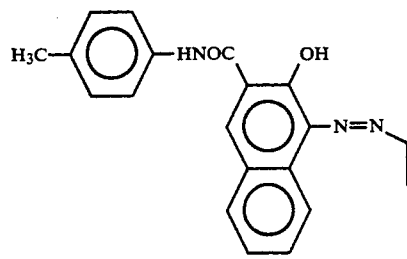

The results of the elemental analysis of the thus obtained bisazo compound (Ic) were as follows:

|  | % C | % H | % N |
|---|---|---|---|
| Calculated | 71.42 | 3.87 | 10.41 |
| Found | 71.27 | 3.78 | 10.30 | having formula (I-2a) was replaced by 0.74 g (2.5 mmol) of 2-hydroxy-3-(3-chlorophenyl)carbamoylnaphthalene (I-3b), so that a bisazo compound of formula (Id) according to the present invention was obtained in a 68% yield. The melting point of the thus obtained bisazo compound was 280° C. or more.

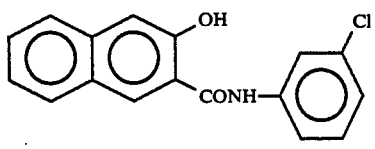

(I-3b)

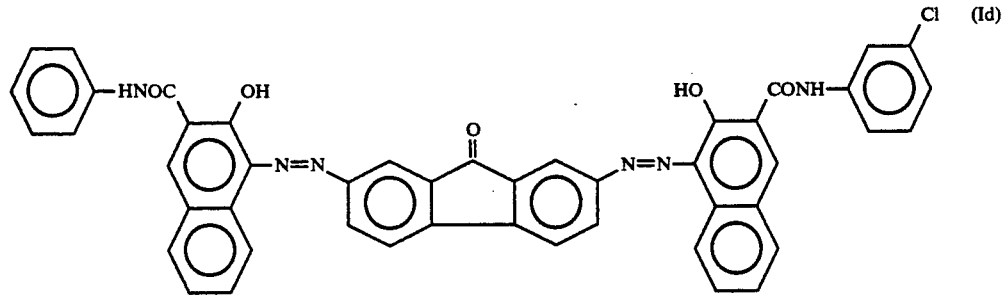

(Id)

The results of the elemental analysis of the thus obtained bisazo compound (Id) were as follows:

|  | % C | % H | % N |
|---|---|---|---|
| Calculated | 71.16 | 3.68 | 10.60 |
| Found | 70.90 | 3.69 | 10.50 |

Figure 4:
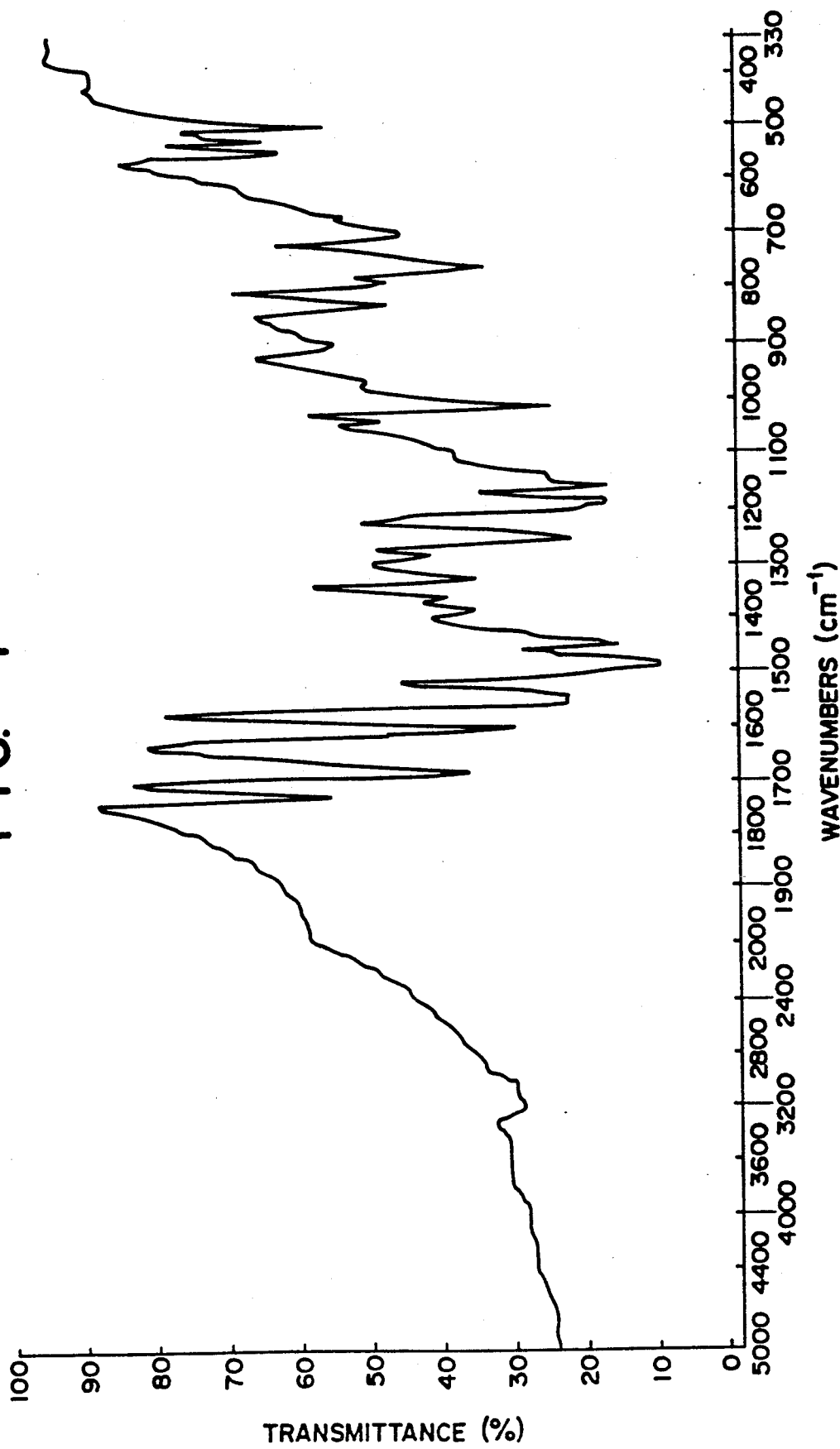

FIG. 4 shows an infrared spectrum of the above obtained bisazo compound, taken by use of a KBr tablet.

EXAMPLE 14

The procedure for preparation of the bisazo compound (Id) used in Example 13 was repeated except that the reaction temperature was changed from the room temperature to a temperature ranging from 10° to 15° C., so that a bisazo compound of formula (Id) according to the present invention was obtained.

EXAMPLE 15

The procedure for preparation of the bisazo compound (Id) used in Example 13 was repeated except that the reaction temperature was changed from the room temperature to a temperature ranging from 0° to 5° C., so that a bisazo compound of formula (Id) according to the present invention was obtained.

EXAMPLE 16

The procedure for preparation of the bisazo compound (Id) used in Example 13 was repeated except that 9-fluorenone-2,7-bisdiazonium bistetrafluoroborate having formula (I-la) was first allowed to react with 2-hydroxy-(3-chlorophenyl)carbamoylnaphthalene (I-3b), and the thus obtained reaction mixture was then allowed to react with -hydroxy-3-phenylcarbamoyl-naphthalene having formula (I-2a), so that a bisazo compound of formula (Id) according to the present invention was obtained.

EXAMPLE 17

0.74 g (2.5 mmol) of 2-hydroxy-3-(2-chlorophenyl)-carbamoylnaphthalene having formula (I-3a) was dissolved in 100 ml of DMF.

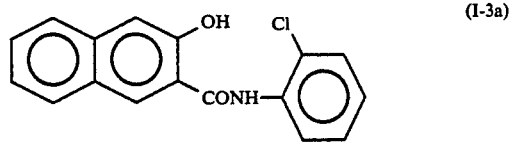

(I-3a)

To the above-prepared solution, 1.02 g (2.5 mmol) of 9-fluorenone-2,7-bisdiazonium bistetrafluoroborate having formula (I-la) was added at room temperature. The reaction mixture was stirred for 10 minutes at room temperature.

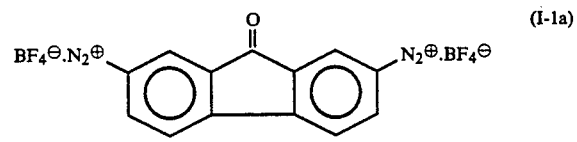

(I-la)

100 ml of DMF solution containing 0.69 g (2.5 mmol) of 2-hydroxy-3-(2-methylphenyl)carbamoylnaphthalene having formula (I-2d) was added to the above reaction mixture, with the addition thereto of 8 ml of 10.5% aqueous solution of sodium acetate, followed by stirring for 2 hours at room temperature.

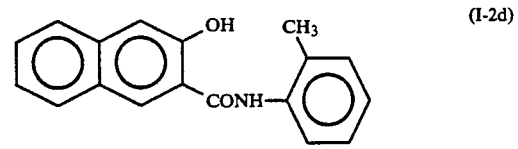

(I-2d)

A precipitated reaction product in the reaction mixture was removed by filtration. The reaction product was washed with 200 ml of DMF of 80° C. three times, and with 200 ml of water twice, and then dried at 120° C. under reduced pressure. Thus, a bisazo compound having formula (Ie) according to the present invention was obtained in a 57% yield. The melting point of the thus obtained bisazo compound was 280° C. or more.

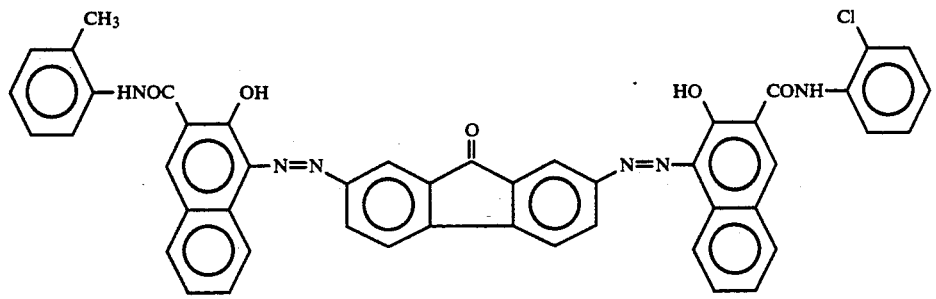

The results of the elemental analysis of the thus obtained bisazo compound (Ie) were as follows:

|  | % C | % H | % N |
|---|---|---|---|
| Calculated | 71.42 | 3.87 | 10.41 |
| Found | 71.28 | 3.98 | 10.24 |

Figure 5:
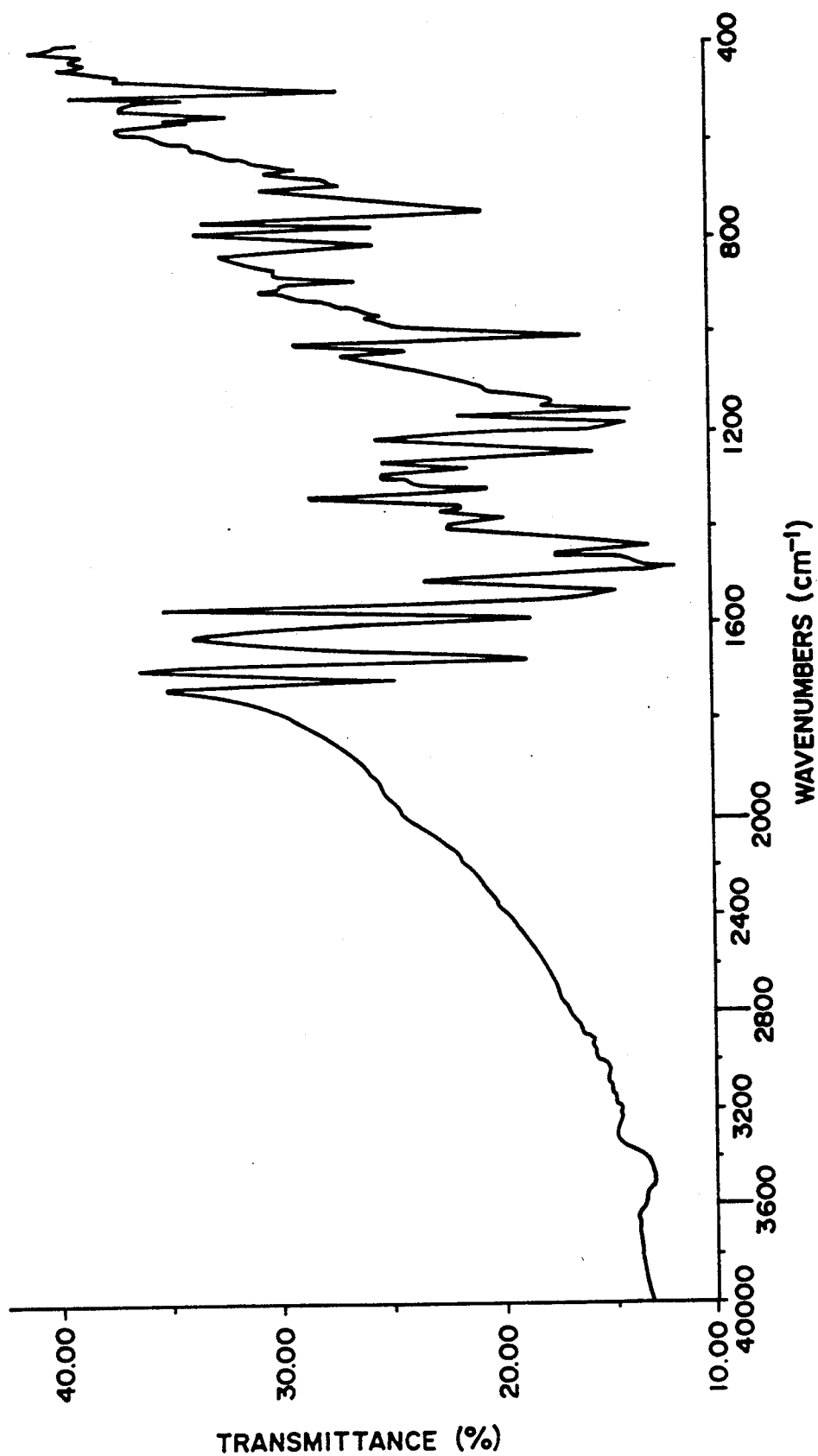

FIG. 5 shows an infrared spectrum of the above obtained bisazo compound, taken by use of a KBr tablet.

EXAMPLE 18

The procedure for preparation of the bisazo compound (Ie) used in Example 17 was repeated except that the reaction temperature was changed from the room temperature to a temperature ranging from 10° to 15° C., so that a bisazo compound of formula (Ie) according to the present invention was obtained.

EXAMPLE 19

The procedure for preparation of the bisazo compound (Ie) used in Example 17 was repeated except that the reaction temperature was changed from the room temperature to a temperature ranging from 0° to 5° C., so that a bisazo compound of formula (Ie) according to the present invention was obtained.

EXAMPLE 20

The procedure for preparation of the bisazo compound (Ie) used in Example 17 was repeated except that 9-fluorenone-2,7-bisdiazonium bistetrafluoroborate having formula (I-1a) was first allowed to react with 2-hydroxy-3-(2-methylphenyl)carbamoylnaphthalene having formula (I-2d), and the thus obtained reaction mixture was then allowed to react with 2-hydroxy-3-(2-chlorophenyl)carbamoylnaphthalene having formula (I-3a), so that a bisazo compound of formula (Ie) according to the present invention was obtained.

EXAMPLE 21

0.74 g (2.5 mmol) of 2-hydroxy-3-(2-chlorophenyl)-carbamoylnaphthalene having formula (I-3a) was dissolved in 100 ml of DMF.

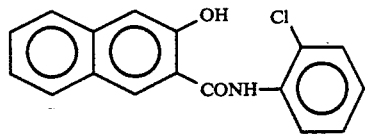

To the above-prepared solution, 1.02 g (2.5 mmol) of 9-fluorenone-2,7-bisdiazonium bistetrafluoroborate having formula (I-1a) was added at room temperature. The reaction mixture was stirred for 10 minutes at room temperature.

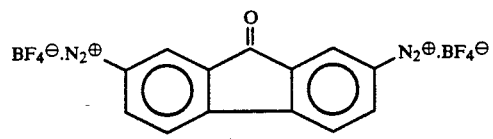

100 ml of DMF solution containing 0.77 g (2.5 mmol) of 2-hydroxy-3-(2-nitrophenyl)carbamoylnaphthalene having formula (I-2e) was added to the above reaction mixture, with the addition thereto of 8 ml of 10.5% aqueous solution of sodium acetate, followed by stirring for 2 hours at room temperature.

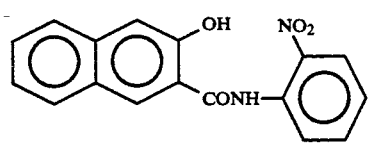

A precipitated reaction product in the reaction mixture was removed by filtration. The reaction product was washed with 200 ml of DMF of 80° C. three times, and with 200 ml of water twice, and then dried at 120° C. under reduced pressure. Thus, a bisazo compound having formula (If) according to the present invention was obtained in a 70% yield. The melting point of the thus obtained bisazo compound was 280° C. or more.

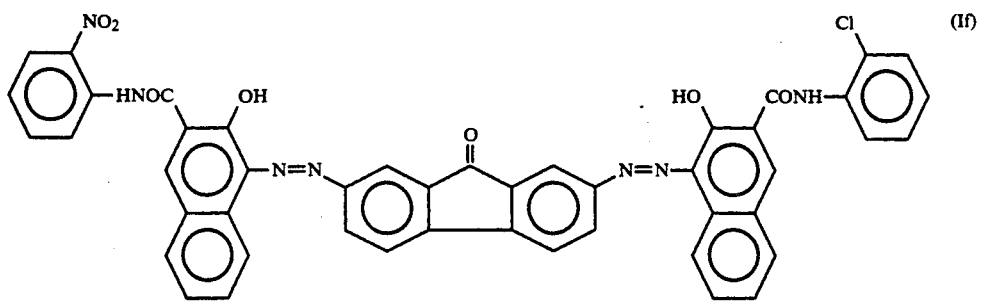

The results of the elemental analysis of the thus obtained bisazo compound (If) were as follows:

|  | % C | % H | % N |
|---|---|---|---|
| Calculated | 67.34 | 3.37 | 11.70 |
| Found | 67.15 | 3.12 | 11.47 |

Figure 6:
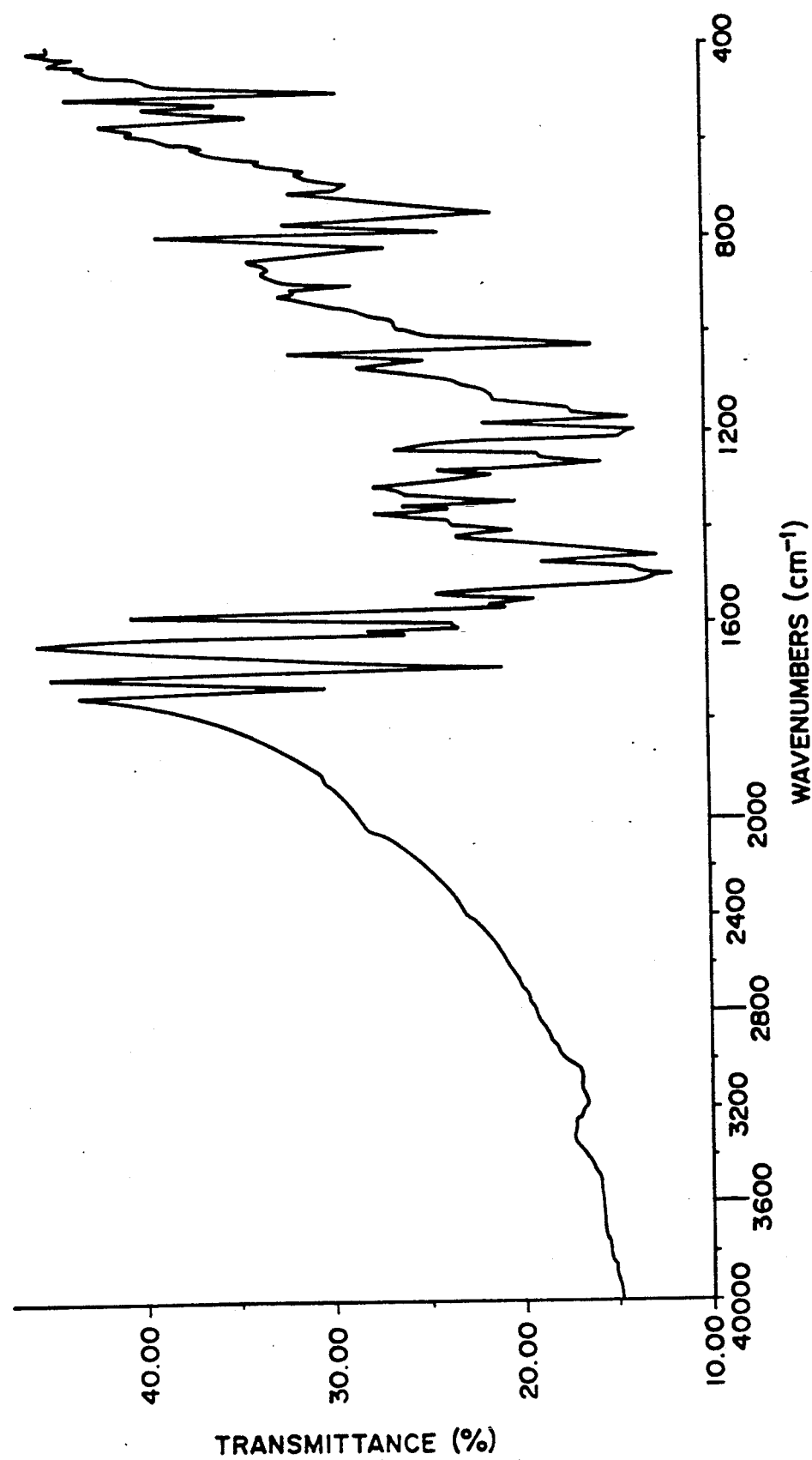

FIG. 6 shows an infrared spectrum of the above obtained bisazo compound, taken by use of a KBr tablet.

EXAMPLE 22

The procedure for preparation of the bisazo compound (If) used in Example 21 was repeated except that the reaction temperature was changed from the room temperature to a temperature ranging from 10° to 15° C., so that a bisazo compound of formula (If) according to the present invention was obtained.

EXAMPLE 23

The procedure for preparation of the bisazo compound (If) used in Example 21 was repeated except that the reaction temperature was changed from the room temperature to a temperature ranging from 0° to 5° C., so that a bisazo compound of formula (If) according to the present invention was obtained.

EXAMPLE 24

The procedure for preparation of the bisazo compound (If) used in Example 21 was repeated except that 9-fluorenone-2,7-bisdiazonium bistetrafluoroborate having formula (I-1a) was first allowed to react with 2-hydroxy-3-(2-nitrophenyl)carbamoylnaphthalene having formula (I-2e), and the thus obtained reaction mixture was then allowed to react with 2-hydroxy-3-(2-chlorophenyl)carbamoylnaphthalene having formula (I-3a), so that a bisazo compound of formula (If) according to the present invention was obtained.

EXAMPLE 25

The procedure for preparation of the bisazo compound (If) used in Example 21 was repeated except that 2-hydroxy-3-(2-nitrophenyl)carbamoylnaphthalene having formula (I-2e) was replaced by 2-hydroxy-3-(3-nitrophenyl)carbamoylnaphthalene having formula (I-2f), so that a bisazo compound having formula (Ig) according to the present invention was obtained in a 61% yield. The melting point of the thus obtained bisazo compound was 280° C. or more.

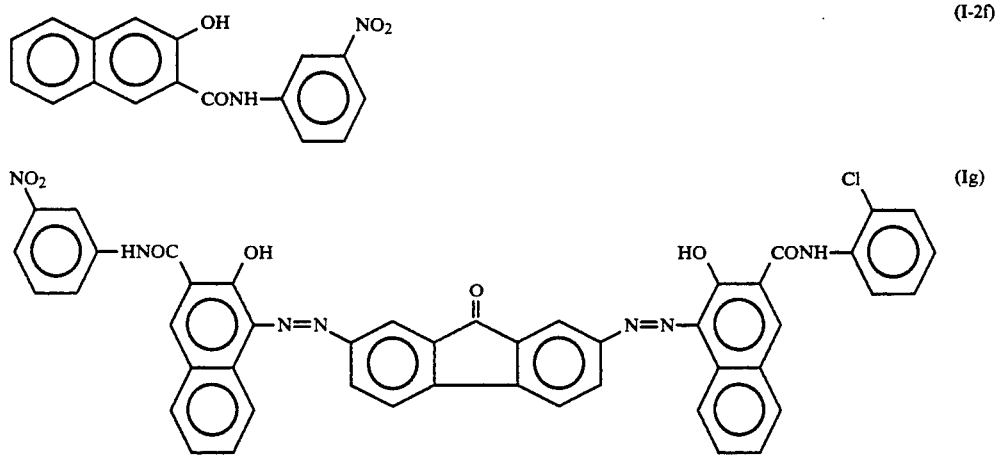

The results of the elemental analysis of the thus obtained bisazo compound (Ig) were as follows:

|  | % C | % H | % N |
|---|---|---|---|
| Calculated | 67.34 | 3.37 | 11.70 |
| Found | 67.32 | 3.57 | 11.47 |

Figure 7:
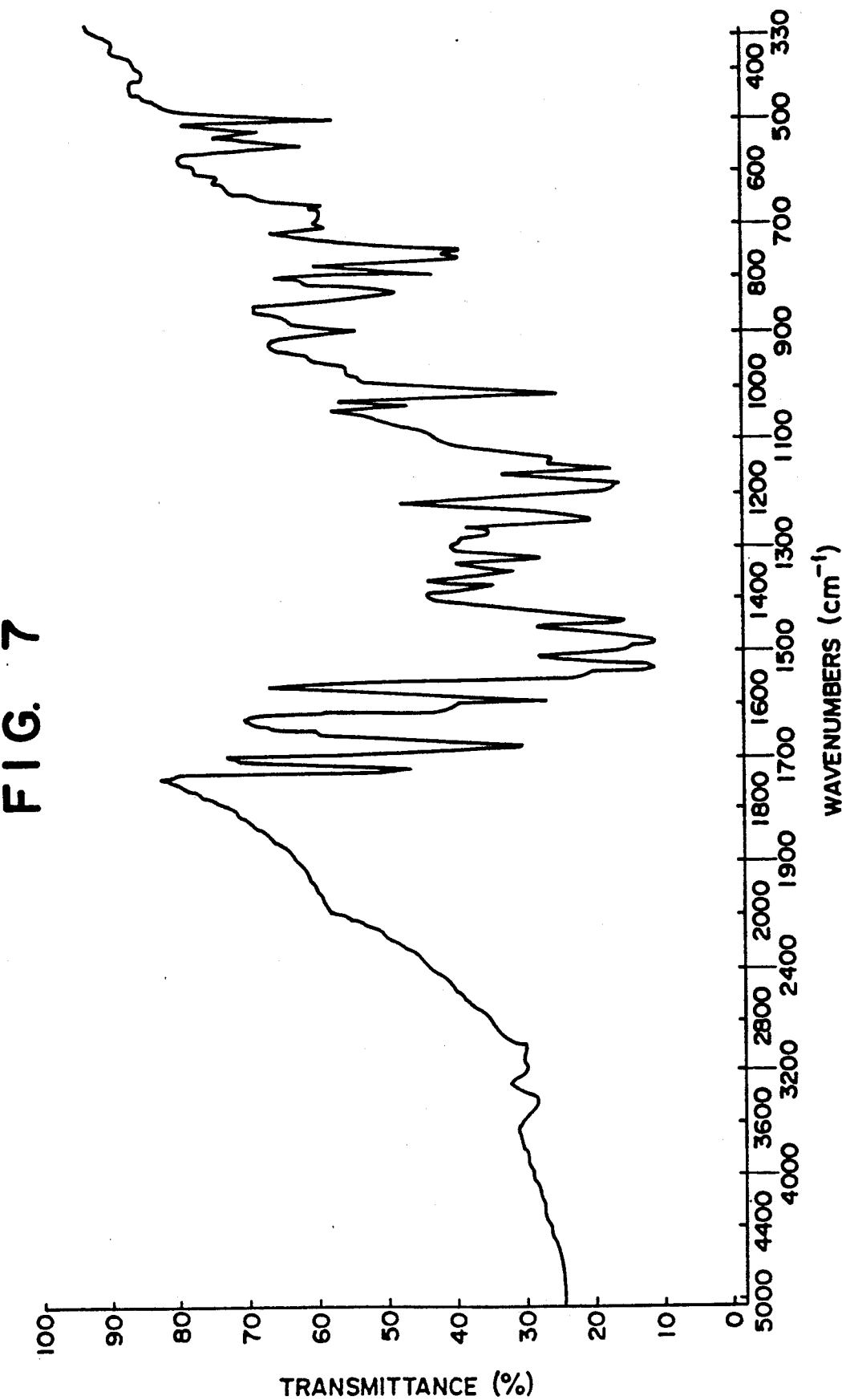

FIG. 7 shows an infrared spectrum of the above obtained bisazo compound, taken by use of a KBr tablet.

EXAMPLE 26

The procedure for preparation of the bisazo compound (Ig) used in Example 25 was repeated except that the reaction temperature was changed from the room temperature to a temperature ranging from 10° to 15° C., so that a bisazo compound of formula (Ig) according to the present invention was obtained.

EXAMPLE 27

The procedure for preparation of the bisazo compound (Ig) used in Example 25 was repeated except that the reaction temperature was changed from the room temperature to a temperature ranging from 0° to 5° C., so that a bisazo compound of formula (Ig) according to the present invention was obtained.

EXAMPLE 28

The procedure for preparation of the bisazo compound (Ig) used in Example 25 was repeated except that 9-fluorenone-2,7-bisdiazonium bistetrafluoroborate having formula (I-1a) was first allowed to react with 2-hydroxy-3-(3-nitrophenyl)carbamoylnaphthalene having formula (I-2f), and the thus obtained reaction mixture was then allowed to react with 2-hydroxy-3-(2-chlorophenyl)carbamoylnaphthalene having formula (I-3a), so that a bisazo compound of formula (Ig) according to the present invention was obtained.

EXAMPLE 29

The procedure for preparation of the bisazo compound (If) used in Example 21 was repeated except that 2-hydroxy-3-(2-nitrophenyl)carbamoylnaphthalene having formula (I-2e) was replaced by 2-hydroxy-3-(4-nitrophenyl)carbamoylnaphthalene having formula (I-2g), so that a bisazo compound having formula (Ih) according to the present invention waas obtained in a 61% yield. The melting point of the thus obtained bisazo compound was 280° C. or more.

EXAMPLE 30

The procedure for preparation of the bisazo compound (Ih) used in Example 29 was repeated except that the reaction temperature was changed from the room temperature to a temperature ranging from 10° to 15° C., so that a bisazo compound of formula (Ih) according to the present invention was obtained.

EXAMPLE 31

The procedure for preparation of the bisazo compound (Ih) used in Example 29 was repeated except that the reaction temperature was changed from the room temperature to a temperature ranging from 0° to 5° C., so that a bisazo compound of formula (Ih) according to the present invention was obtained.

EXAMPLE 32

The procedure for preparation of the bisazo compound (Ih) used in Example 29 was repeated except that 9-fluorenone-2,7-bisdiazonium bistetrafluoroborate having formula (I-1a) was first allowed to react with 2-hydroxy-3-(4-nitrophenyl)carbamoylnaphthalene having formula (I-2g), and the thus obtained reaction mixture was then allowed to react with 2-hydroxy-3-(2-chlorophenyl)carbamoylnaphthalene having formula (I-3a), so that a bisazo compound of formula (Ih) according to the present invention was obtained

EXAMPLE 33

The procedure for preparation of the bisazo compound (If) used in Example 21 was repeated except that 0.77 g (2.5 mmol) of 2-hydroxy-3-(2-nitrophenyl)carbamoylnaphthalene having formula (I-2e) was replaced by 0.73 g (2.5 mmol) of 2-hydroxy-3-(4-methoxyphenyl)carbamoylnaphthalene having formula (I-2h), so that a bisazo compound having formula (Ii) according to the present invention was obtained in a 54% yield. The melting point of the thus obtained bisazo compound was 280° C. or more.

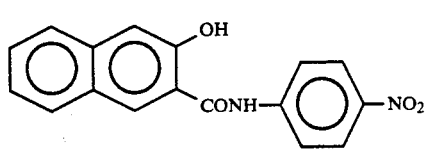

(I-2g)

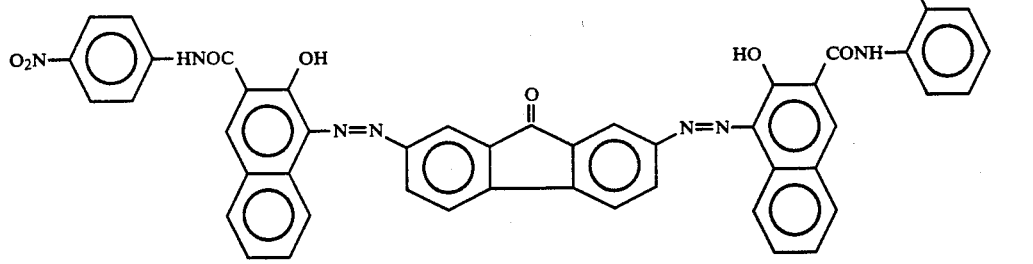

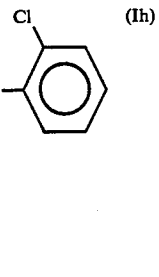

(Ih)

The results of the elemental analysis of the thus obtained bisazo compound (Ih) were as followed:

|  | % C | % H | % N |
|---|---|---|---|
| Calculated | 67.34 | 3.37 | 11.70 |
| Found | 67.31 | 3.28 | 11.45 |

Figure 8:
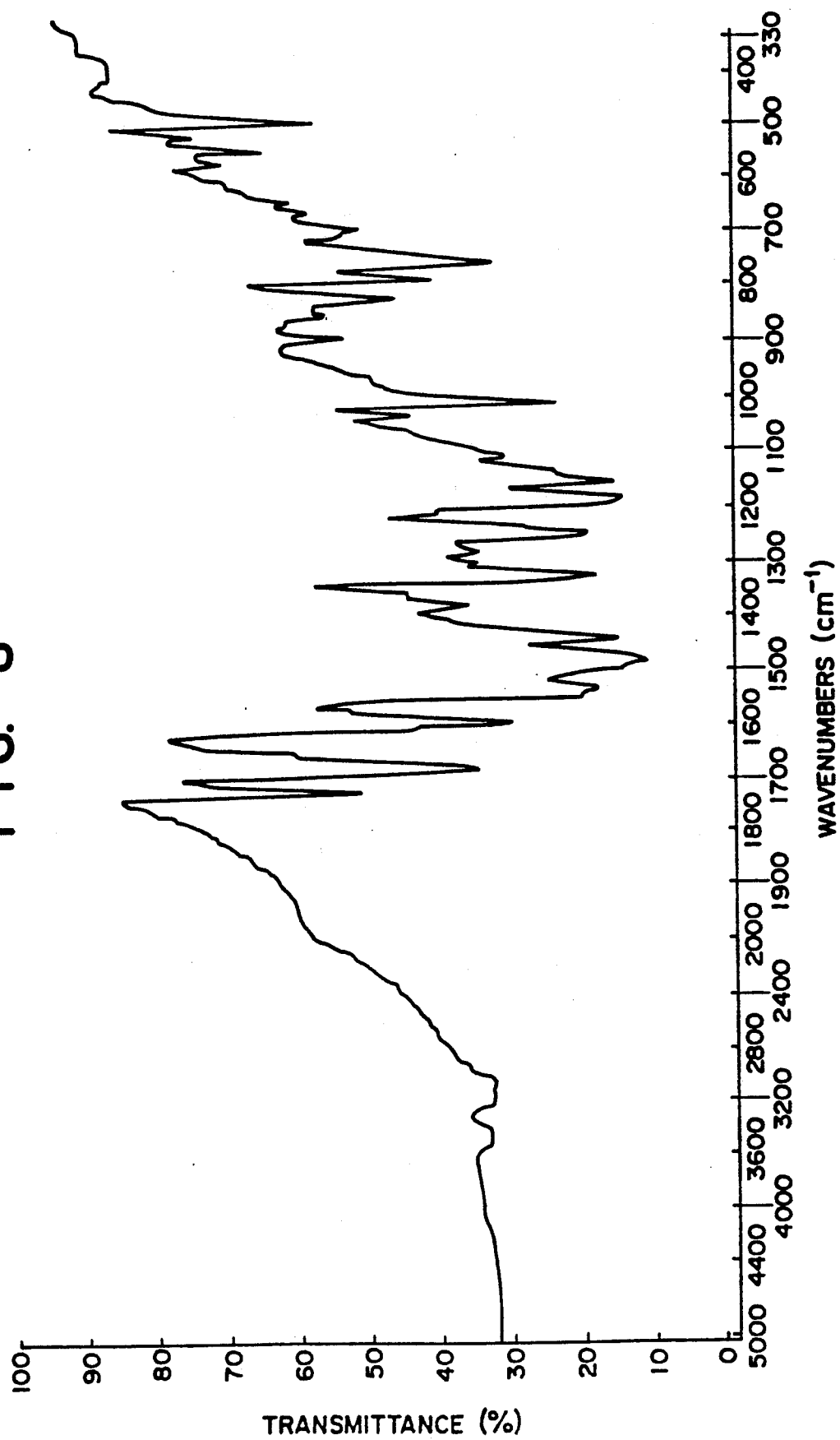

FIG. 8 shows an infrared spectrum of the above obtained bisazo compound, taken by use of a KBr tablet

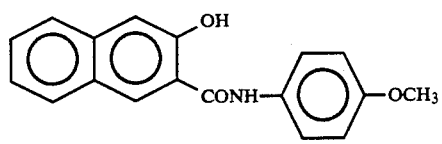

(I-2h)

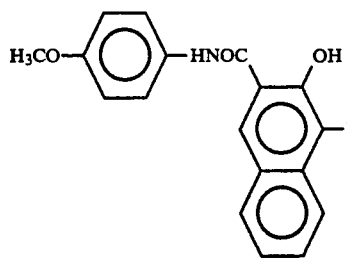
(Ii)

The results of the elemental analysis of the thus obtained bisazo compound (Ii) were as follows:

|  | % C | % H | % N |
|---|---|---|---|
| Calculated | 70.02 | 3.80 | 10.21 |
| Found | 69.76 | 3.55 | 10.10 |

Figure 9:
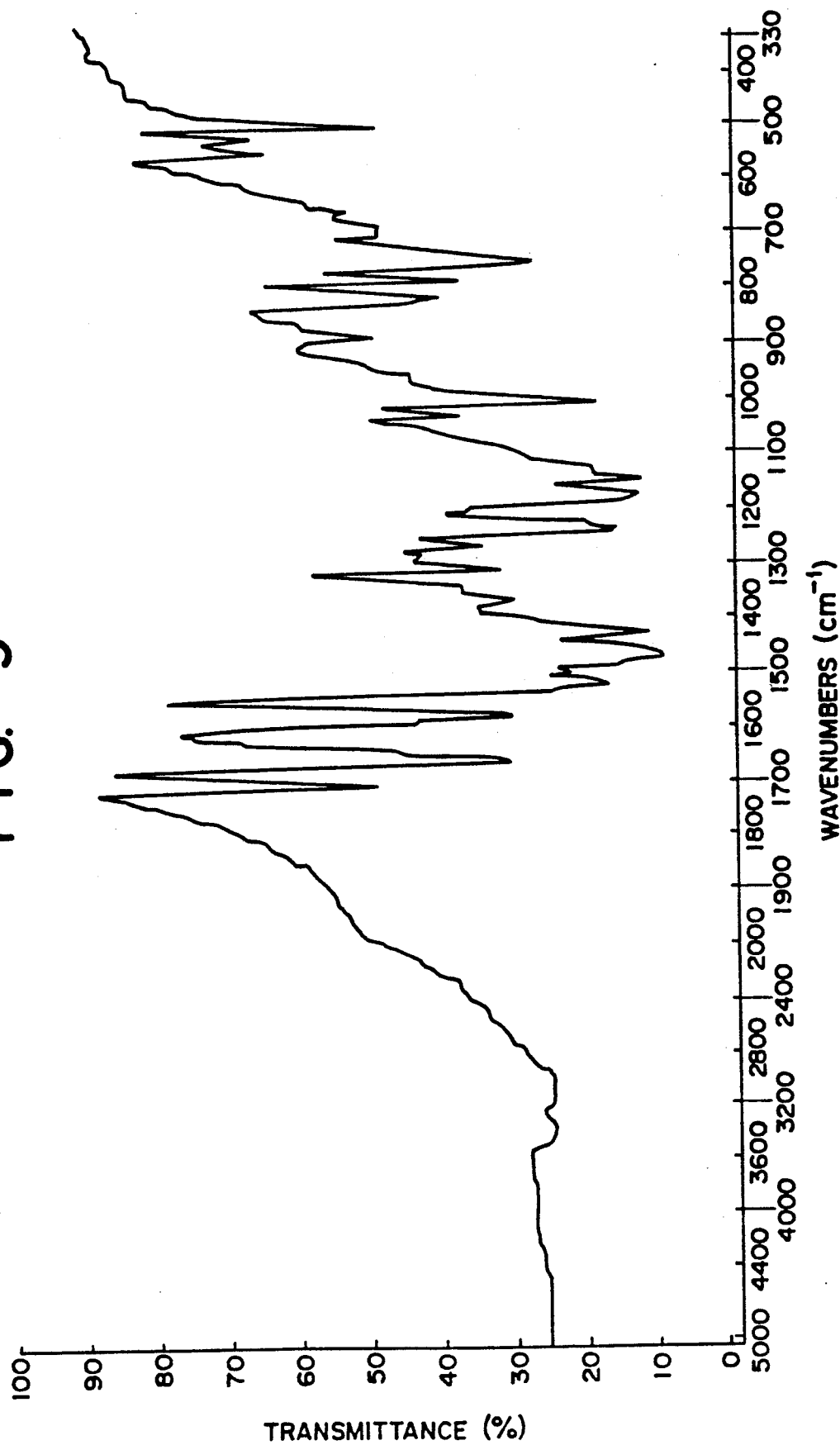

FIG. 9 shows an infrared spectrum of the above obtained bisazo compound, taken by use of a KBr tablet

EXAMPLE 34

The procedure for preparation of the bisazo compound (Ii) used in Example 33 was repeated except that

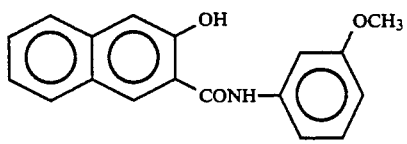
(I-2i)

the reaction temperature was changed from the room temperature to a temperature ranging from 10° to 15° C., so that a bisazo compound of formula (Ii) according to the present invention was obtained.

EXAMPLE 35

The procedure for preparation of the bisazo compound (Ii) used in Example 33 was repeated except that the reaction temperature was changed from the room temperature to a temperature ranging from 0° to 5° C., so that a bisazo compound of formula (Ii) according to the present invention was obtained.

EXAMPLE 36

The procedure for preparation of the bisazo compound (Ii) used in Example 33 was repeated except that 9-fluorenone-2,7-bisdiazonium bistetrafluoroborate having formula (I-1a) was first allowed to react with 2-hydroxy-3-(4-methoxyphenyl)carbamoylnaphthalene having formula (I-2h), and the thus obtained reaction mixture was then allowed to react with 2-hydroxy-3-(2-chlorophenyl)carbamoylnaphthalene having formula (I-3a), so that a bisazo compound of formula (Ii) according to the present invention was obtained.

EXAMPLE 37

The procedure for preparation of the bisazo compound (Ii) used in Example 33 was repeated except that 2-hydroxy-3-(4-methoxyphenyl)carbamoylnaphthalene having formula (I-2h) was replaced by 2-hydroxy-3-(3-methoxyphenyl)carbamoylnaphthalene having formula (I-2i), so that a bisazo compound having formula (Ij) according to the present invention was obtained in a 53% yield. The melting point of the thus obtained bisazo compound was 280° C. or more.

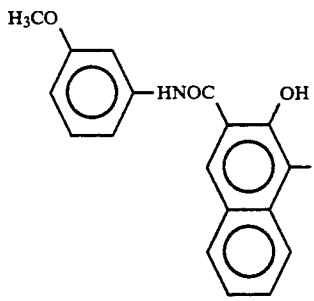

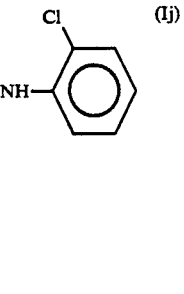
(Ij)

The results of the elemental analysis of the thus obtained bisazo compound (Ij) were as follows:

|  | % C | % H | % N |
|---|---|---|---|
| Calculated | 70.02 | 3.80 | 10.21 |
| Found | 69.98 | 3.50 | 10.05 |

Figure 10:
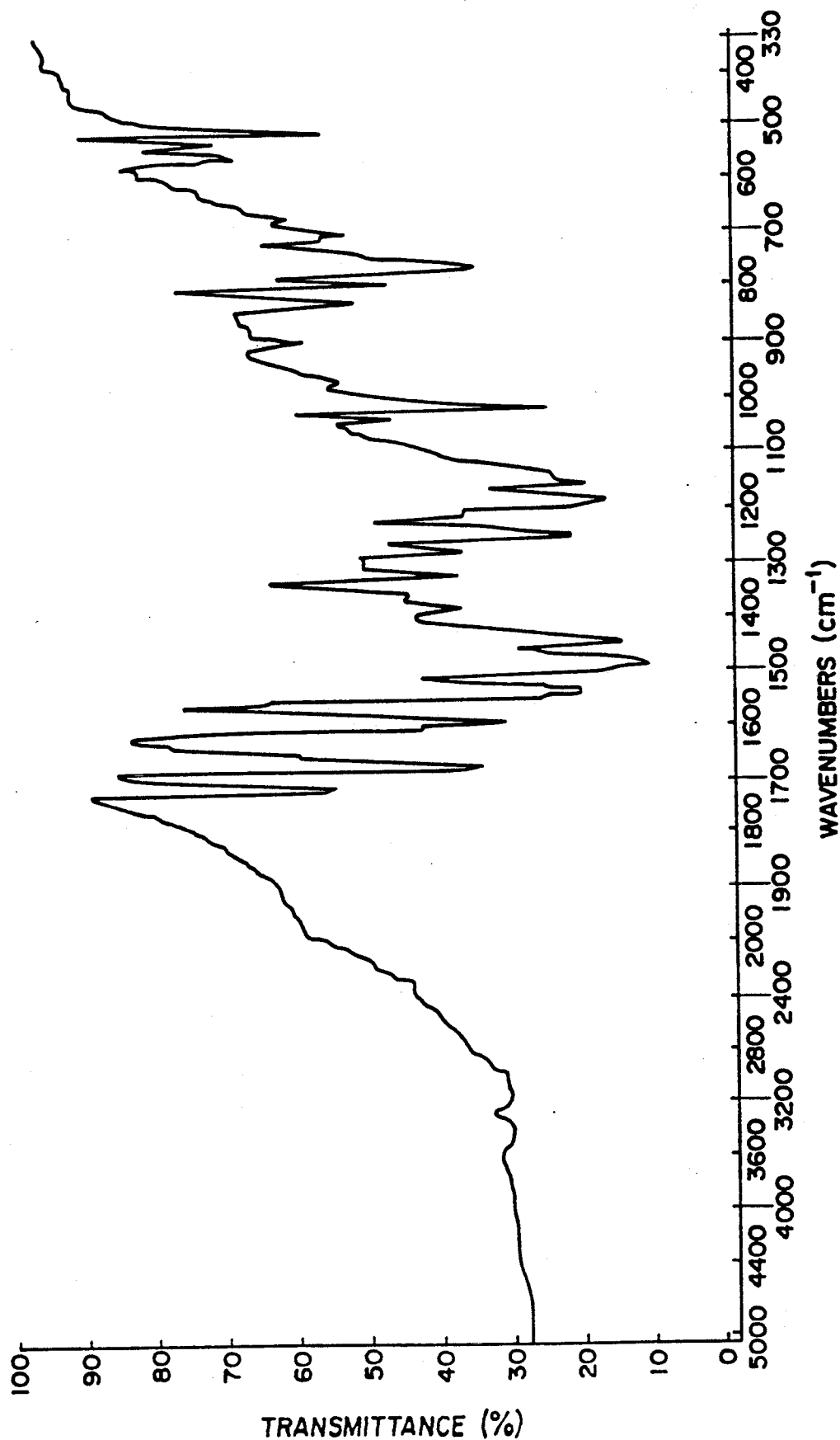

FIG. 10 shows an infrared spectrum of the above obtained bisazo compound, taken by use of a KBr tablet.

EXAMPLE 38

The procedure for preparation of the bisazo compound (Ij) used in Example 37 was repeated except that the reaction temperature was changed from the room temperature to a temperature ranging from 10° to 15° C., so that a bisazo compound of formula (Ij) according to the present invention was obtained.

EXAMPLE 39

The procedure for preparation of the bisazo compound (Ij) used in Example 37 was repeated except that the reaction temperature was changed from the room temperature to a temperature ranging from 0° to 5° C., so that a bisazo compound of formula (Ij) according to the present invention was obtained.

EXAMPLE 40

The procedure for preparation of the bisazo compound (Ij) used in Example 37 was repeated except that 9-fluorenone-2,7-bisdiazonium bistetrafluoroborate having formula (I-1a) was first allowed to react with 2-hydroxy-3-(3-methoxyphenyl)carbamoylnaphthalene having formula (I-2i), and the thus obtained reaction mixture was then allowed to react with 2-hydroxy-3-(2-chlorophenyl)carbamoylnaphthalene having formula (I-3a), so that a bisazo compound of formula (Ij) according to the present invention was obtained.

EXAMPLE 41

The procedure for preparation of the bisazo compound (Ii) used in Example 33 was repeated except that 2-hydroxy-3-(4-methoxyphenyl)carbamoylnaphthalene having formula (I-2h) was replaced by 2-hydroxy-3-(2-methoxyphenyl)carbamoylnaphthalene having formula (I-2j), so that a bisazo compound having formula (Ik) according to the present invention was obtained in a 60% yield. The melting point of the thus obtained bisazo compound was 280° C. or more.

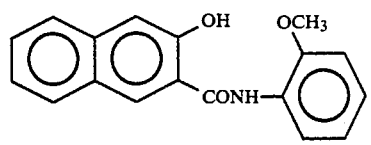
(I-2j)

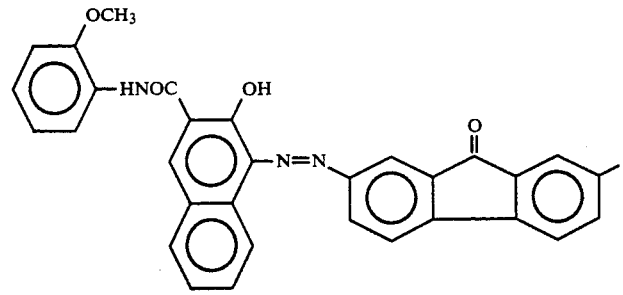
(Ik)

The results of the elemental analysis of the thus obtained bisazo compound (Ik) were as follows:

|  | % C | % H | % N |
|---|---|---|---|
| Calculated | 70.02 | 3.80 | 10.21 |
| Found | 69.75 | 3.55 | 10.10 |

Figure 11:
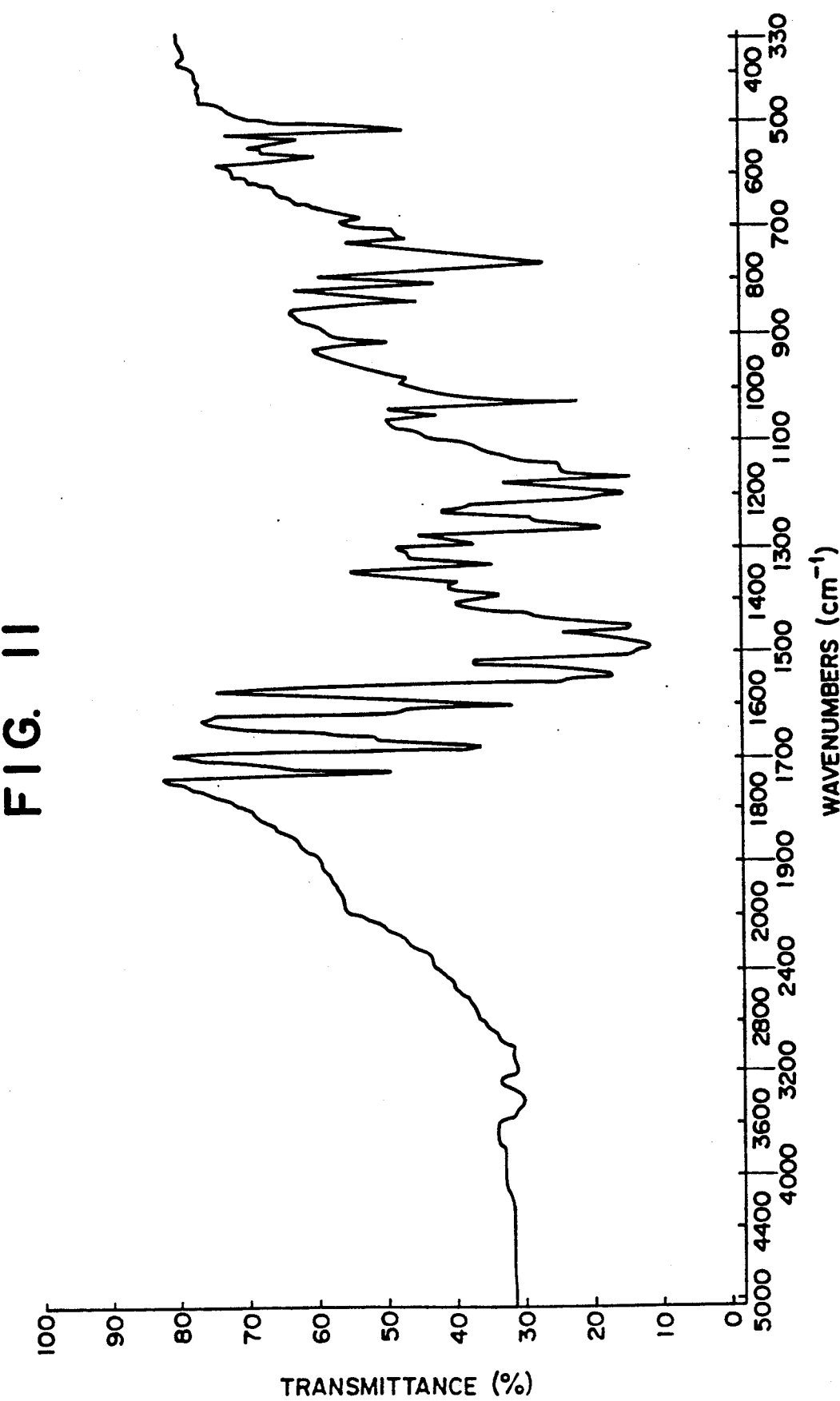

FIG. 11 shows an infrared spectrum of the above obtained bisazo compound, taken by use of a KBr tablet.

EXAMPLE 42

The procedure for preparation of the bisazo compound (Ik) used in Example 41 was repeated except that the reaction temperature was changed from the room temperature to a temperature ranging from 10° to 15° C., so that a bisazo compound of formula (Ik) according to the present invention was obtained.

EXAMPLE 43

The procedure for preparation of the bisazo compound (Ik) used in Example 41 was repeated except that the reaction temperature was changed from the room temperature to a temperature ranging from 0° to 5° C., so that a bisazo compound of formula (Ik) according to the present invention was obtained.

EXAMPLE 44

The procedure for preparation of the bisazo compound (Ik) used in Example 41 was repeated except that 9-fluorenone-2,7-bisdiazonium bistetrafluoroborate having formula (I-1a) was first allowed to react with 2-hydroxy-3-(2-methoxyphenyl)carbamoylnaphthalene having formula (I-2j), and the thus obtained reaction mixture was then allowed to react with 2-hydroxy-3-(2-chlorophenyl)carbamoylnaphthalene having formula (I-3a), so that a bisazo compound of formula (Ik) according to the present invention was obtained.

EXAMPLE 45

0.66 g (2.5 mmol) of 2-hydroxy-3-phenylcarbamoylnaphthalene having formula (I-2a) was dissolved in 100 ml of DMF.

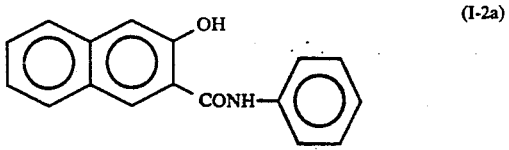
(I-2a)

To the above-prepared solution, 1.02 g (2.5 mmol) of 9-fluorenone-2,7-bisdiazonium bistetrafluoroborate having formula (I-1a) was added at room temperature. The reaction mixture was stirred for 10° minutes at room temperature.

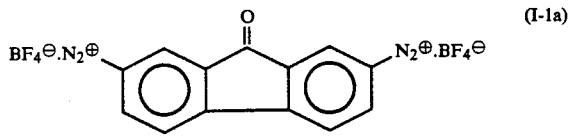
(I-1a)

100 ml of DMF solution containing 0.74 g (2.5 mmol) of 2-hydroxy-3-(4-chlorophenyl)carbamoylnaphthalene having formula (I-3c) was added to the above reaction mixture, with the addition thereto of 8 ml of 10.5% aqueous solution of sodium acetate, followed by stirring for 2 hours at room temperature.

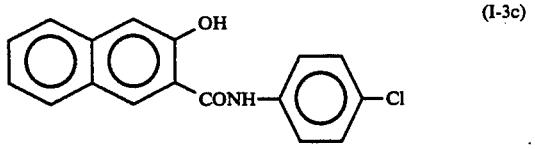
(I-3c)

A precipitated reaction product in the reaction mixture was removed by filtration. The reaction product was washed with 200 ml of DMF of 80° C. three times, and with 200 ml of water twice, and then dried at 120° C. under reduced pressure. Thus, a bisazo compound having formula (I1) according to the present invention was obtained in a 59% yield. The melting point of the thus obtained bisazo compound was 280° C. or more.

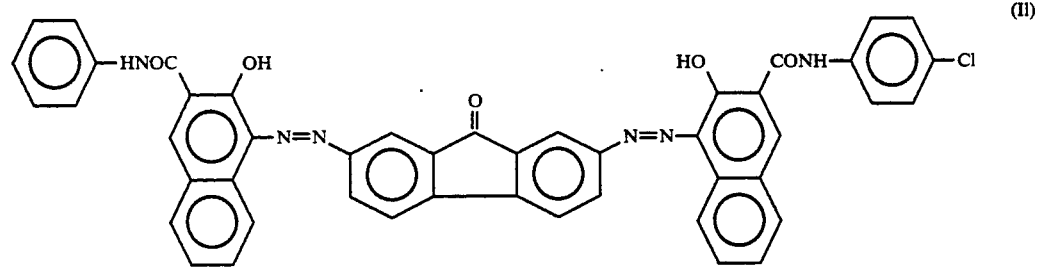
(I1)

The results of the elemental analysis of the thus obtained bisazo compound (I1) were as follows:

|  | % C | % H | % N |
|---|---|---|---|
| Calculated | 71.16 | 3.68 | 10.60 |
| Found | 71.11 | 3.52 | 10.73 |

Figure 12:
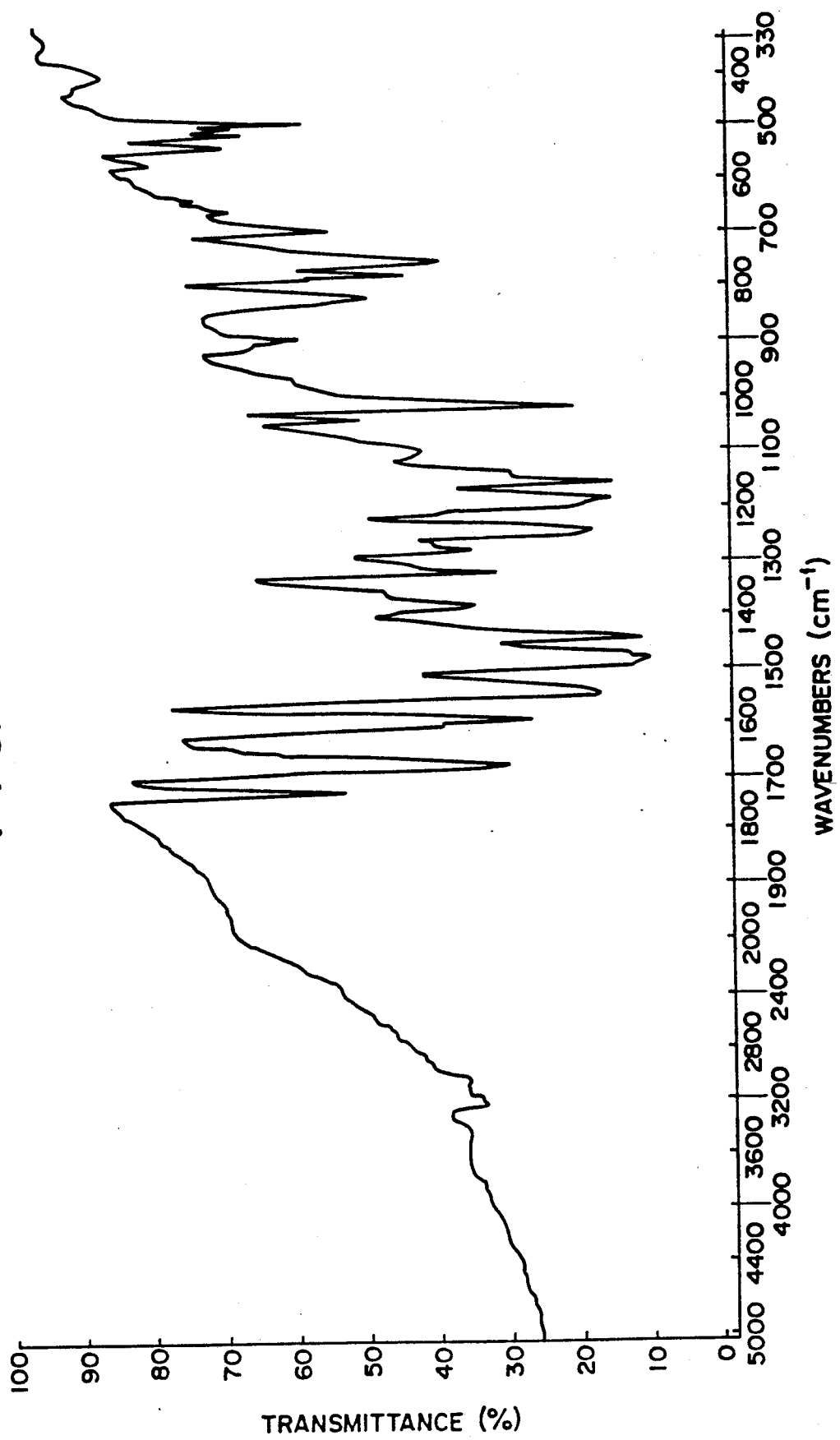

FIG. 12 shows an infrared spectrum of the above obtained bisazo compound, taken by use of a KBr tablet.

EXAMPLE 46

The procedure for preparation of the bisazo compound (II) used in Example 45 was repeated except that the reaction temperature was changed from the room temperature to a temperature ranging from 10° to 15° C., so that a bisazo compound of formula (II) according to the present invention was obtained.

EXAMPLE 47

The procedure for preparation of the bisazo compound (II) used in Example 45 was repeated except that the reaction temperature was changed from the room temperature to a temperature ranging from 0° to 5° C., so that a bisazo compound of formula (II) according to the present invention was obtained.

EXAMPLE 48

The procedure for preparation of the bisazo compound (II) used in Example 45 was repeated except that 9-fluorenone-2,7-bisdiazonium bistetrafluoroborate having formula (I-1a) was first allowed to react with 2-hydroxy-3-(4-chlorophenyl)carbamoylnaphthalene having formula (I-3c), and the thus obtained reaction mixture was then allowed to react with 2-hydroxy-3-phenylcarbamoylnaphthalene having formula (I-2a), so that a bisazo compound of formula (I1) according to the present invention was obtained.

EXAMPLE 49

0.74 g (2.5 mmol) of 2-hydroxy-3-(2-chlorophenyl)carbamoylnaphthalene having formula (II-3) was dissolved in 100 ml of DMF.

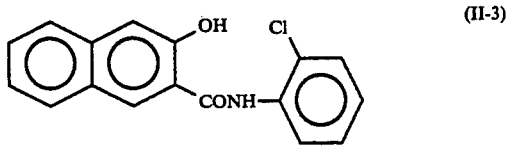
(II-3)

To the above-prepared solution, 1.02 g (2.5 mmol) of 9-fluorenone-2,7-bisdiazonium bistetrafluoroborate having formula (II-1a) was added at room temperature.

The reaction mixture was stirred for 10 minutes at room temperature.

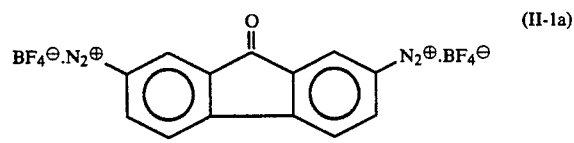
(II-1a)

100 ml of DMF solution containing 0.74 g (2.5 mmol) of 2-hydroxy-3-(3-chlorophenyl)carbamoylnaphthalene having formula (II-2a) was added to the above reaction mixture, with the addition thereto of 8 ml of 10.5% aqueous solution of sodium acetate, followed by stirring for 2 hours at room temperature.

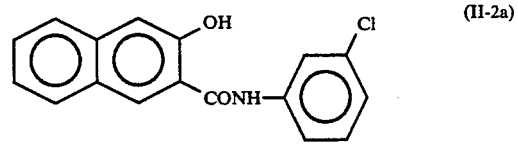
(II-2a)

A precipitated reaction product in the reaction mixture was removed by filtration. The reaction product was washed with 200 ml of DMF of 80° C. three times, and with 200 ml of water twice, and then dried at 120° C. under reduced pressure. Thus, a bisazo compound having formula (IIa) according to the present invention was obtained in a 70% yield. The melting point of the thus obtained bisazo compound was 280° C. or more.

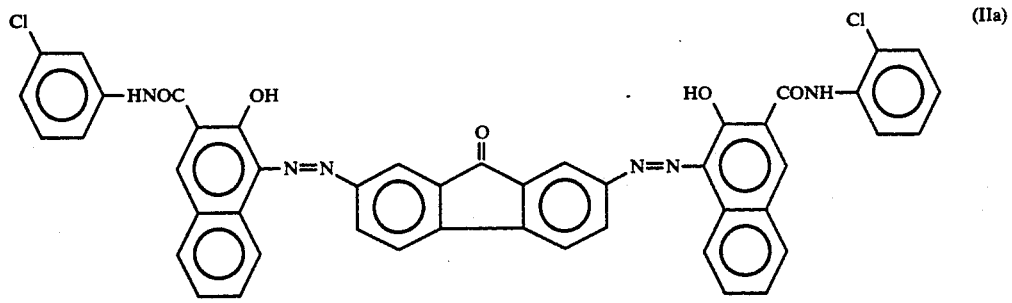
(IIa)

The results of the elemental analysis of the thus obtained bisazo compound (IIa) were as follows:

|  | % C | % H | % N |
|---|---|---|---|
| Calculated | 68.21 | 3.41 | 10.15 |
| Found | 67.99 | 3.25 | 10.04 |

Figure 13:
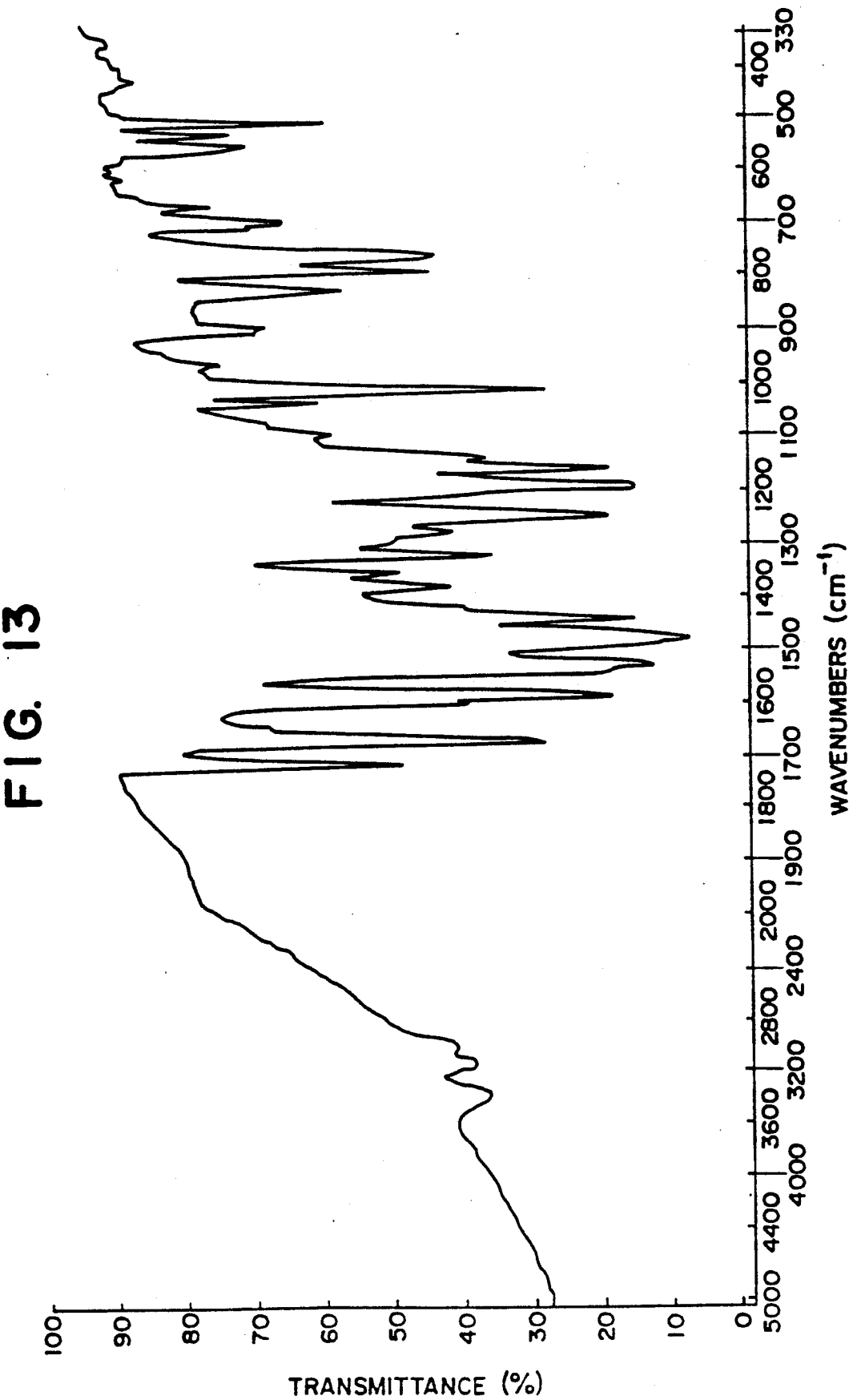

FIG. 13 shows an infrared spectrum of the above obtained bisazo compound, taken by use of a KBr tablet.

EXAMPLE 50

The procedure for preparation of the bisazo compound (IIa) used in Example 49 was repeated except that the reaction temperature was changed from the room temperature to a temperature ranging from 10° to 15° C., so that a bisazo compound of formula (IIa) according to the present invention was obtained.

EXAMPLE 51

The procedure for preparation of the bisazo compound (IIa) used in Example 49 was repeated except that the reaction temperature was changed from the room temperature to a temperature ranging from 0° to 5° C., so that a bisazo compound of formula (IIa) according to the present invention was obtained.

EXAMPLE 52

The procedure for preparation of the bisazo compound (IIa) used in Example 49 was repeated except that -fluorenone-2,7-bisdiazonium bistetrafluoroborate having formula (II-1a) was first allowed to react with 2-hydroxy-3-(3-chlorophenyl)carbamoylnaphthalene having formula (II-2a), and the thus obtained reaction mixture was then allowed to react with 2-hydroxy-3-(2-chlorophenyl)carbamoylnaphthalene having formula (II-3), so that a bisazo compound of formula (IIa) according to the present invention was obtained.

EXAMPLE 53

The procedure for preparation of the bisazo compound (IIa) used in Example 49 was repeated except that 2-hydroxy-3-(3-chlorophenyl)carbamoylnaphthalene having formula (II-2a) was replaced by 2-hydroxy-3-(4-chlorophenyl)carbamoylnaphthalene having formula (II-2b), so that a bisazo compound having formula (IIb) according to the present invention was obtained in a 53% yield. The melting point of the thus obtained bisazo compound was 280° C. or more.

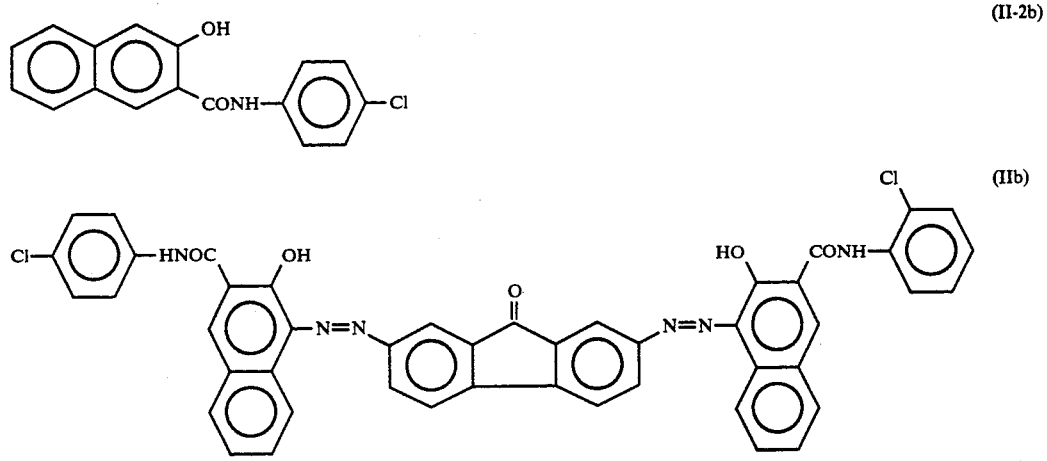
(II-2b)

(IIb)

The results of the elemental analysis of the thus obtained bisazo compound (IIb) were as follows:

|  | % C | % H | % N |
|---|---|---|---|
| Calculated | 68.20 | 3.41 | 10.15 |
| Found | 67.86 | 3.53 | 10.08 |

Figure 14:
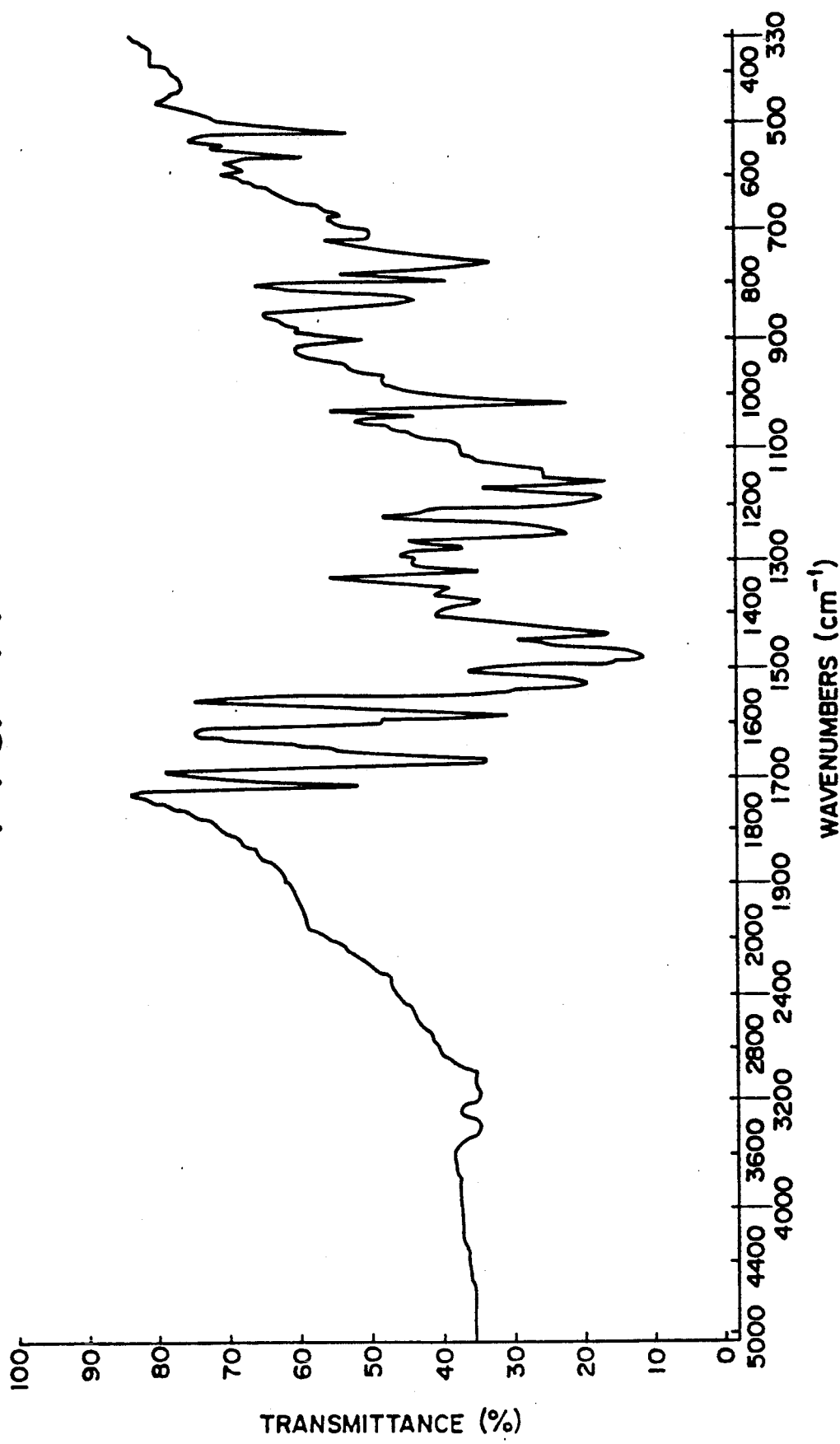

FIG. 14 shows an infrared spectrum of the above obtained bisazo compound, taken by use of a KBr tablet.

EXAMPLE 54

The procedure for preparation of the bisazo compound (IIb) used in Example 53 was repeated except that the reaction temperature was changed from the room temperature to a temperature ranging from 10° to 15° C., so that a bisazo compound of formula (IIb) according to the present invention was obtained.

EXAMPLE 55

The procedure for preparation of the bisazo compound (IIb) used in Example 53 was repeated except that the reaction temperature was changed from the room temperature to a temperature ranging from 0° to 5° C., so that a bisazo compound of formula (IIb) according to the present invention was obtained.

EXAMPLE 56

The procedure for preparation of the bisazo compound (IIb) used in Example 53 was repeated except that 9-fluorenone-2,7-bisdiazonium bistetrafluoroborate having formula (II-1a) was first allowed to react with 2-hydroxy-3-(4-chlorophenyl)carbamoylnaphthalene having formula (II-2b), and the thus obtained reaction mixture was then allowed to react with 2-hydroxy-3-(2-chlorophenyl)carbamoylnaphthalene having formula (II-3), so that a bisazo compound of formula (IIb) according to the present invention was obtained.

APPLICATION EXAMPLE 1

76 parts by weight of the bisazo compound (Ia) obtained in Example 1 serving as a charge generating material, 1260 parts by weight of a 2% tetrahydrofuran solution of a polyester resin (Trademark "Vylon 200", made by Toyobo Company, Ltd.) and 3700 parts by weight of tetrahydrofuran were dispersed and ground in a ball mill. The thus prepared dispersion was ooated on an aluminum surface of an aluminum-deposited polyester film serving as an electroconductive support by a doctor blade, and dried at room temperature, so that a charge generation layer with a thickness of about 1 $\mu$m was formed on the aluminum-deposited polyester film.

2 parts by weight of 4'-N,N-diphenylamino-$\alpha$-phenylstilbene serving as a charge transporting material, 2 parts by weight of polycarbonate resin (Trademark "Panlite K-1300", made by Teijin Limited ) and 16 parts by weight of tetrahydrofuran were mixed to form a solution. This solution was coated on the above formed charge generation layer by a doctor blade, and then dried at 80° C. for 2 minutes and then at 105° C. for 5 minutes, so that a charge transport layer with a thickness of about 20 $\mu$m was formed on the charge generation layer. Thus, a two-layered type electrophotographic photoconductor was obtained.

The above-mentioned photoconductor was negatively charged in the dark by using a corona charger until the surface potential of the photoconductor exceeded $-800$ V. The photoconductor was then allowed to stand in the dark without applying any charge thereto until the surface potential thereof reached $-800$ V. When the surface potential reached $-800$ V, a monochromatic light having an intensity of 1 $\mu$W/cm$^2$ on the surface of the photoconductor was applied thereto by a monochrometer. The time (sec) required to reduce the surface potential of $-800$ V to $-400$ V was measured and the exposure ($\mu$W.sec/cm$^2$) required to reduce the initial surface potential ($-800$ V) to $\frac{1}{2}$ the initial surface potential was calculated.

From the apparent potential difference of 400 V, which appeared to be obtained by the exposure, the decrease in the potential caused by a decay corresponding to the dark decay in the course of the exposure was subtracted, thereby obtaining the actual potential difference. Using the thus obtained actual potential difference and the exposure required to reduce the initial surface potential to $\frac{1}{2}$ the initial surface potential, the spectral sensitivity (volt·cm$^2$·$\mu$J$^{-1}$) was calculated, and the spectral sensitivity curve as shown in FIG. 15 was obtained.

Figure 15:
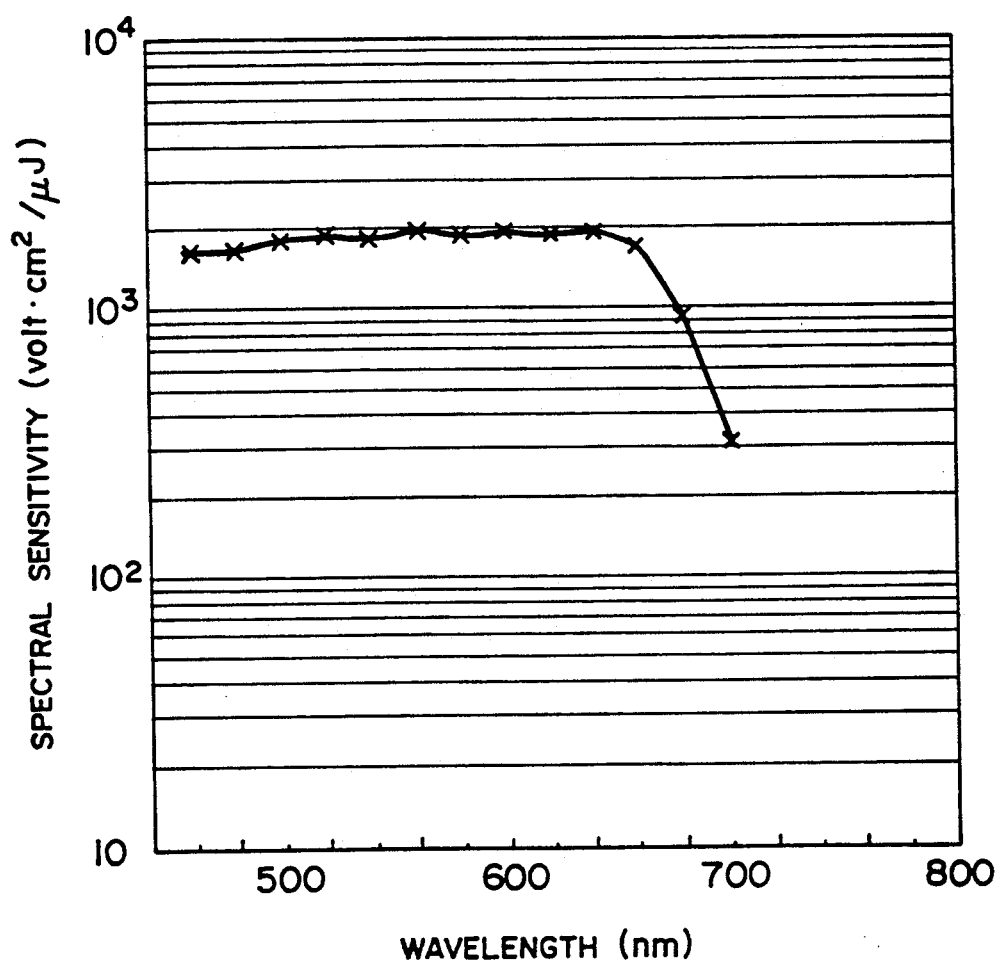
FIG. 15 is a spectral sensitivity curve of a photoconductor obtained in Application Example 1.

As is apparent from the spectral sensitivity curve as shown in FIG. 15, the sensitivity of the electrophotographic photoconductor of two-layered type comprising the bisazo compound of the present invention is remarkably excellent.

APPLICATION EXAMPLE 2

Figure 16:
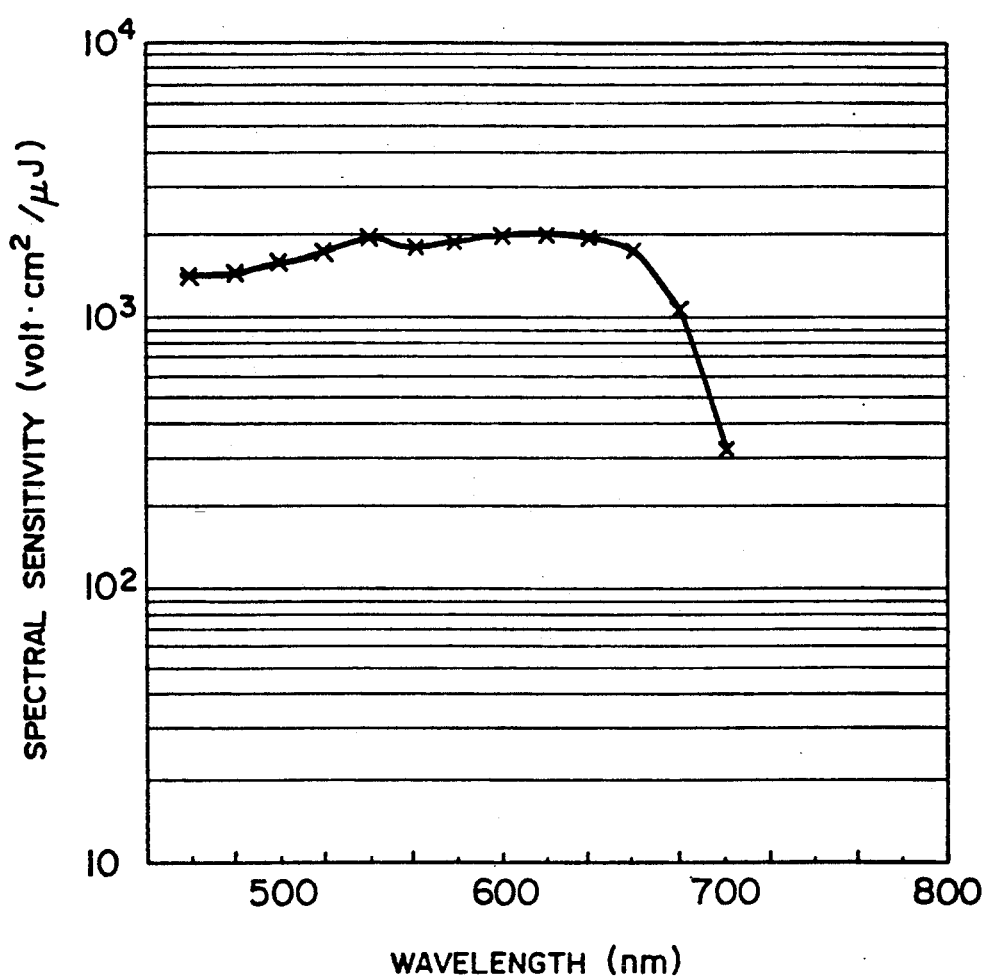
FIGS. 16 to 20 are spectral sensitivity curves of photoconductors obtained in Application Examples 2, 3, 4, 13 and 14, respectively.

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (Ib) obtained in Example 5. Thus, the electrophotographic photoconductor of two-layered type comprising the bisazo compound according to the present invention was obtained FIG. 16 shows the spectral sensitivity curve of the thus obtained photoconductor, which is obtained in the same manner as in Application Example 1. As is aprent from the spectral sensitivity curve as shown in FIG. 16, the sensitivity of the photoconductor is excellent.

APPLICATION EXAMPLE 3

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (Ic) obtained in Example 9. Thus, the electrophotographic photoconductor of two-layered type comprising the bisazo compound according to the present invention was obtained.

Figure 17:
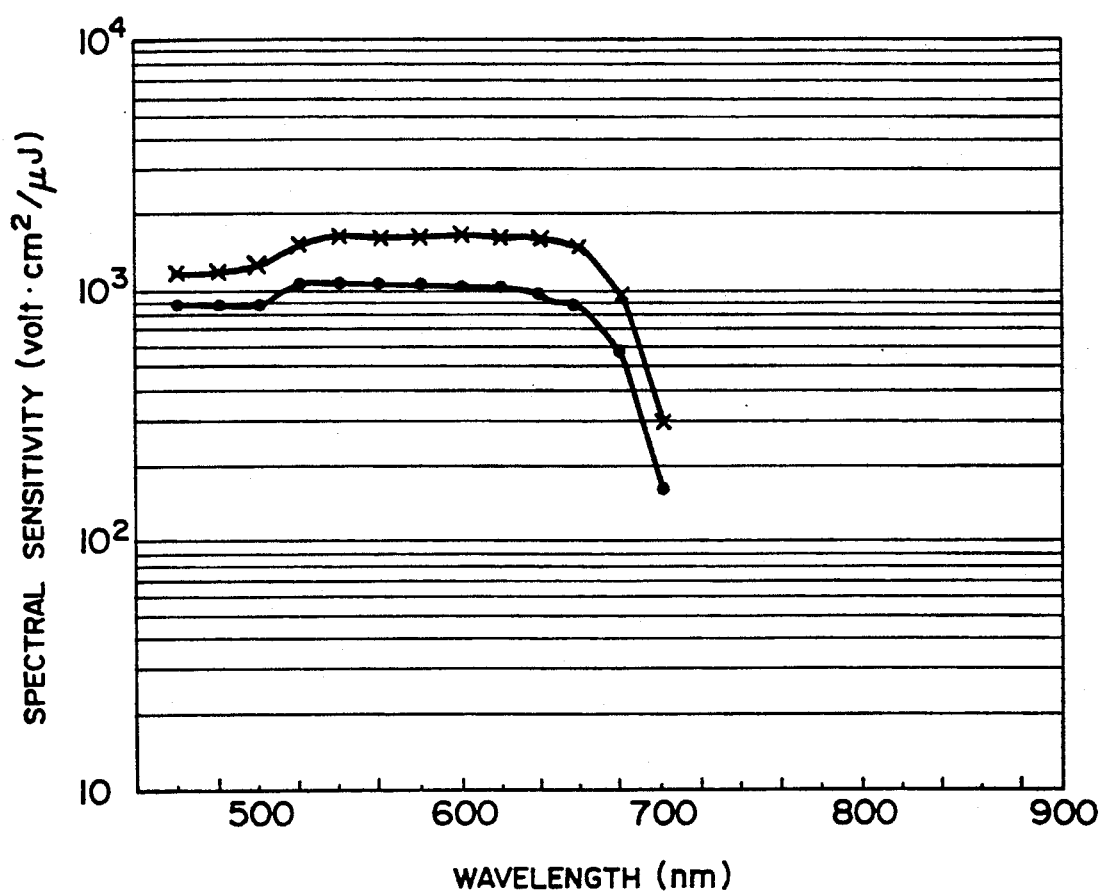

FIG. 17 shows the spectral sensitivity curve of the thus obtained photoconductor, which is obtained in the same manner as in Application Example 1. As is aprent from the spectral sensitivity curve as shown in FIG. 17, the sensitivity of the photoconductor is excellent.

APPLICATION EXAMPLE 4

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (Id) obtained in Example 13. Thus, the electrophotogra-phic photoconductor of two-layered type comprising the bisazo compound according to the present invention was obtained.

Figure 18:
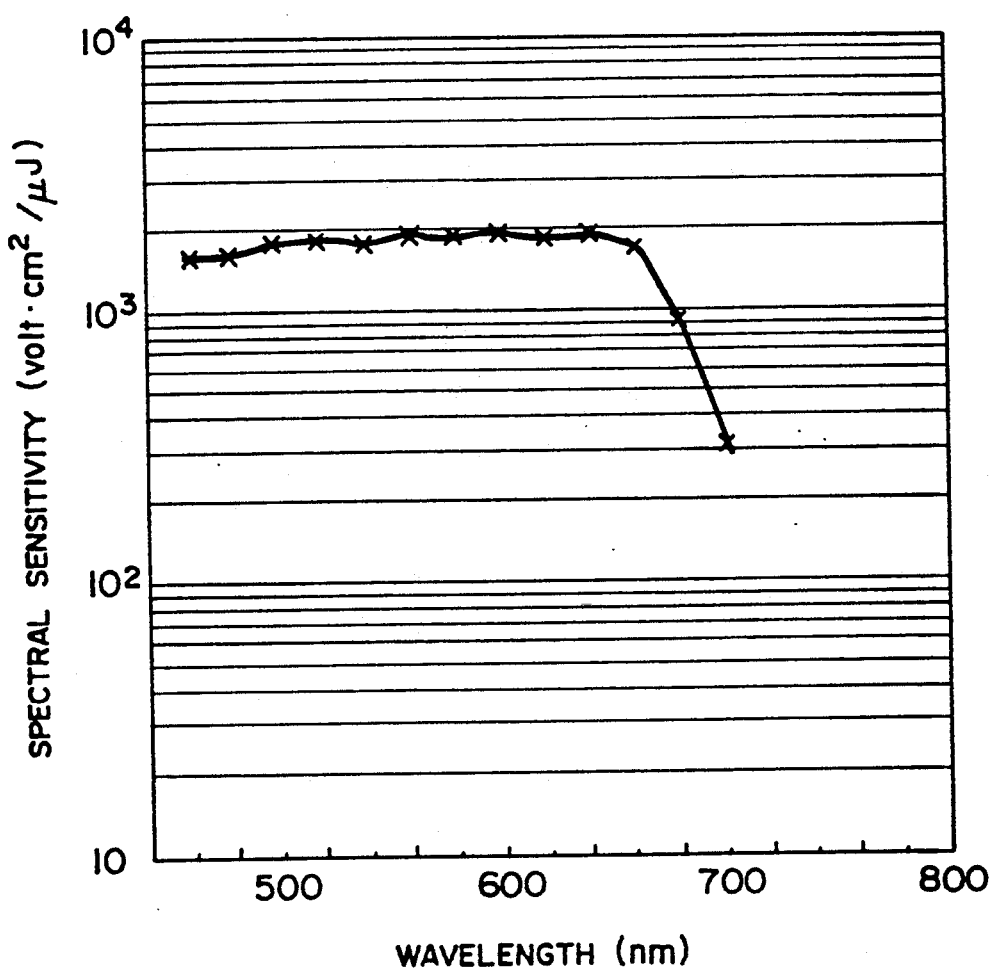

FIG. 18 shows the spectral sensitivity curve of the thus obtained photoconductor, which is obtained in the same manner as in Application Example 1. As is aprent from the spectral sensitivity curve as shown in FIG. 18, the sensitivity of the photoconductor is excellent.

APPLICATION EXAMPLE 5

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (Ie) obtained in Example 17. Thus, the electrophotographic photoconductor of two-layered type comprising the bisazo compound according to the present invention was obtained

APPLICATION EXAMPLE 6

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (If) obtained in Example 21, and that 4'-N,N-diphenylamino-α-phenylstilbene serving as a charge transporting material for use in the charge transport layer in Application Example 1 was replaced by 1-phenyl-3-(4-diethylamino)styryl-5-(4-diethylamino)-phenylpyrazoline. Thus, the electrophotographic photoconductor of two-layered type comprising the bisazo compound according to the present invention was obtained.

APPLICATION EXAMPLE 7

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (Ig) obtained in Example 25. Thus, the electrophotogra-ohic photoconductor of two-layered type comprising the bisazo compound according to the present invention was obtained

APPLICATION EXAMPLE 8

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (Ih) obtained in Example 29. Thus, the electrophotographic photoconductor of two-layered type comprising the bisazo compound according to the present invention was obtained.

APPLICATION EXAMPLE 9

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (Ii) obtained in Example 33. Thus, the electrophotographic photoconductor of two-layered type comprising the bisazo compound according to the present invention was obtained.

APPLICATION EXAMPLE 10

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (Ij) obtained in Example 37. Thus, the electrophotographic photoconductor of two-layered type comprising the bisazo compound according to the present invention was obtained.

APPLICATION EXAMPLE 11

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (Ik) obtained in Example 41, and that 4'-N,N-diphenylamino-α-phenylstilbene serving as a charge transporting material for use in the charge transport layer in Application Example 1 was replaced by 9-ethylcarbazole-3-aldehyde-1-methyl-1-phenylhydrazone. Thus, the electrophotogra-phic photoconductor of two-layered type comprising the bisazo compound according to the present invention was obtained.

APPLICATION EXAMPLE 12

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (Il) obtained in Example 45. Thus, the electrophotographic photoconductor of two-layered type comprising the bisazo compound according to the present invention was obtained.

Each of the electrophotographic photoconductors thus obtained in Application Examples 5 to 12 was negatively charged in the dark under application of −6 kV of corona charge for 20 seconds, using a commercially available electrostatic copying sheet testing apparatus ("Paper Analyzer Model SP-428", made by Kawaguchi Electro Works Co., Ltd.). The photoconductor was then allowed to stand in the dark for 20 seconds without applying any charge thereto, and the surface potential Vpo (V) of the photoconductor was measured. The photoconductor was then illuminated by a tungsten lamp in such a manner that the illuminance on the illuminated surface of the photoconductor was 4.5 lux, and the exposure $E_{\frac{1}{2}}$(lux·sec) required to reduce the initial surface potential Vpo (V) to ½ the initial surface potential Vpo (V) was measured. The results are given in Table 1.

TABLE 1

| Application Example No. | Vpo (V) | $E_{\frac{1}{2}}$ (lux · sec) |
|---|---|---|
| 5 | −1076 | 0.7 |
| 6 | −1076 | 0.7 |
| 7 | −960 | 0.9 |
| 8 | −758 | 0.8 |
| 9 | −1156 | 1.0 |
| 10 | −1046 | 0.7 |
| 11 | −628 | 0.8 |
| 12 | −1454 | 2.3 |

APPLICATION EXAMPLE 13

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (IIa) obtained in Example 49. Thus, the electrophotographic photoconductor of two-layered type comprising the bisazo compound according to the present invention was obtained.

Figure 19:
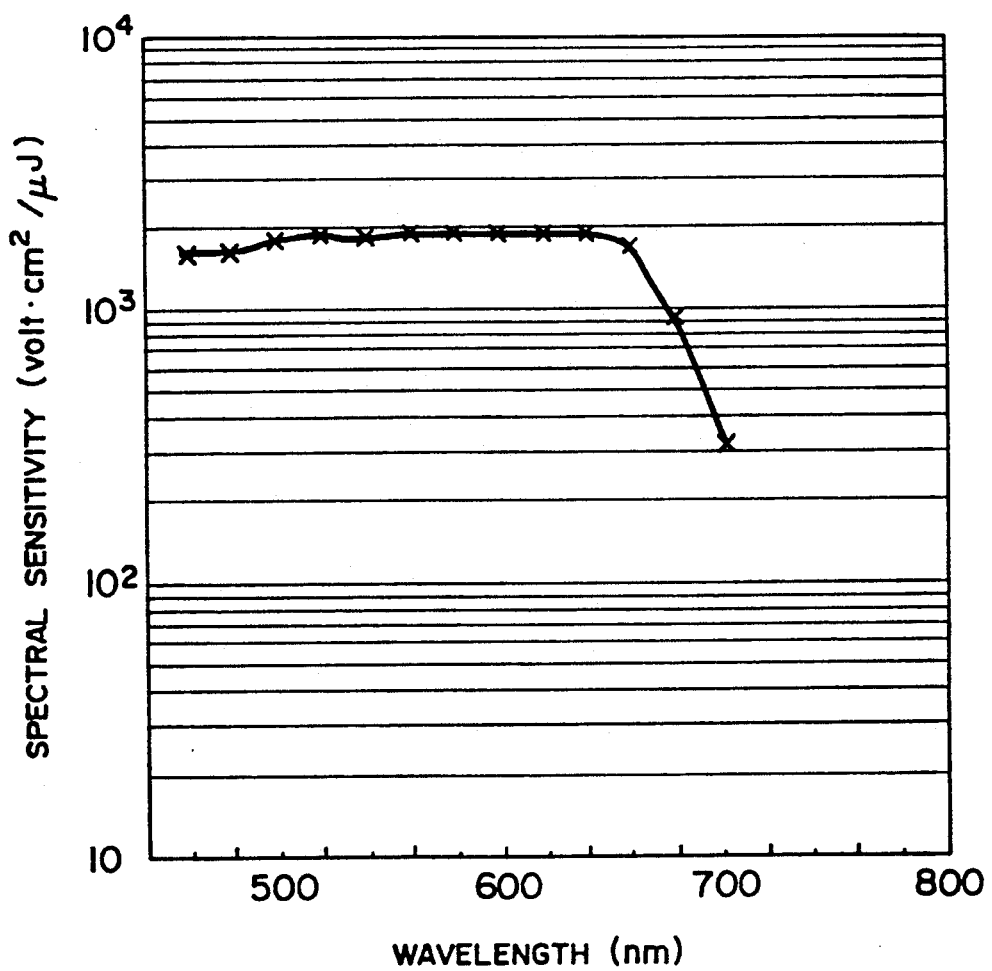

FIG. 19 shows the spectral sensitivity curve of the thus obtained photoconductor, which is obtained in the same manner as in Application Example 1. As is apprent from the spectral sensitivity curve as shown in FIG. 19, the sensitivity of the photoconductor is excellent.

APPLICATION EXAMPLE 14

The procedure for preparation of the two-layered type electrophotographic photoconductor used in Application Example 1 was repeated except that the bisazo compound (Ia) obtained in Example 1 serving as a charge generating material for use in the charge generation layer in Application Example 1 was replaced by the bisazo compound (IIb) obtained in Example 53. Thus, the electrophotographic photoconductor of two-layered type comprising the bisazo compound according to the present invention was obtained.

Figure 20:
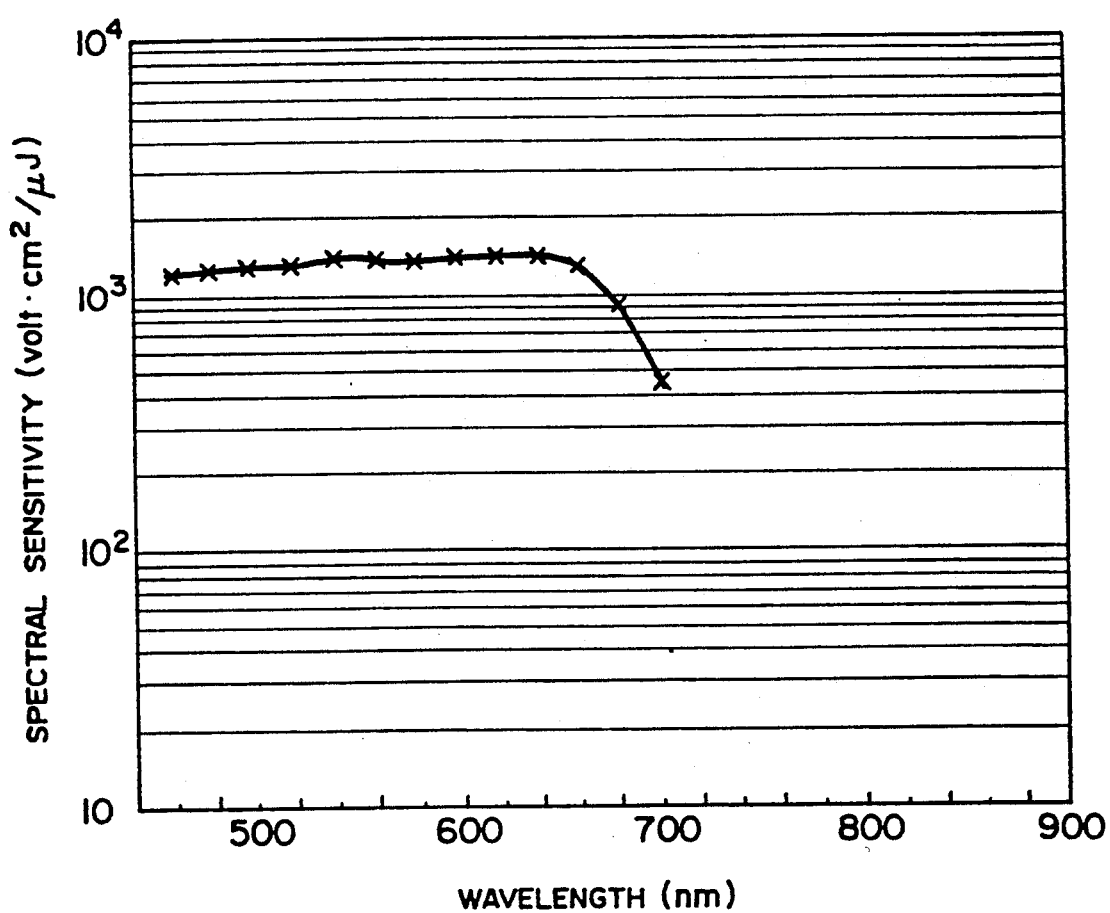

FIG. 20 shows the spectral sensitivity curve of the thus obtained photoconductor, which is obtained in the same manner as in Application Example 1. As is apprent from the spectral sensitivity curve as shown in FIG. 20, the sensitivity of the photoconductor is excellent.

As previously described, the bisazo compounds according to the present invention can easily be prepared. In addition, the bisazo compounds of the present invention are remarkably useful as charge generating materials for use in the two-layered type electrophotographic photoconductor, that is, the practical photoconductor with high sensitivity suitable for high-speed copying apparatus.

What is claimed is:

1. A bisazo compound selected from the group consisting of

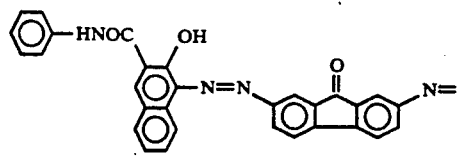

and

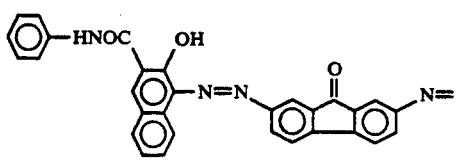

2. The bisazo compound as claimed in claim 1, represented by formula:

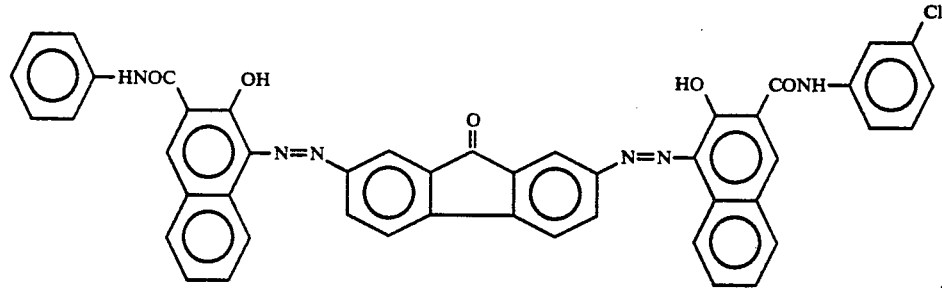

3. The bisazo compound as claimed in claim 1, represented by formula:

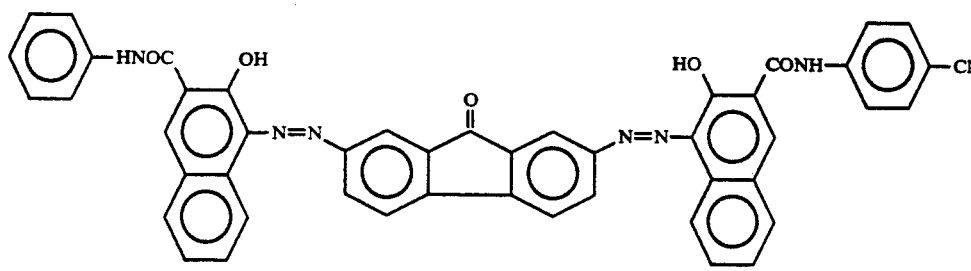

* * * * *

UNITED STATES PATENT AND TRADEMARK OFFICE
CERTIFICATE OF CORRECTION

PATENT NO. : 5,317,093

DATED : May 31, 1994

INVENTOR(S) : HASHIMOTO

It is certified that error appears in the above-identified patent and that said Letters Patent is hereby corrected as shown below:

Column 17, line 32, "(Ia}" should read --(Ia)--.

Column 19, line 60, "-hydroxy" should read --2-hydroxy--.

Column 25, line 29, "waas" should read --was--.

Column 27, line 24, after "tablet" insert --.--.

Column 30, line 60, "10°" delete --°--.

UNITED STATES PATENT AND TRADEMARK OFFICE
CERTIFICATE OF CORRECTION

PATENT NO. : 5,317,093
DATED : May 31, 1994
INVENTOR(S) : HASHIMOTO

It is certified that error appears in the above-identified patent and that said Letters Patent is hereby corrected as shown below:

Column 35, line 29, "ooated" should read --coated--.

Column 36, line 20, after "obtained" insert --.--.

Column 36, line 52, "electrophotogra-phic", should read
                    --electrophotographic--.

Column 37, line 30, "electrophotogra-ohic", should read
                    --electrophotographic"

Column 38, line 14, "electrophotogra-phic", should read
                    --electrophotographic"

Signed and Sealed this

Thirteenth Day of June, 1995

Attest:

BRUCE LEHMAN

Attesting Officer    Commissioner of Patents and Trademarks